United States Patent [19]
Beckett et al.

[11] Patent Number: 5,908,851
[45] Date of Patent: Jun. 1, 1999

[54] DERIVATIVES OF SUCCINAMIDE AND THEIR USE AS METALLOPROTEINASE INHIBITOR

[75] Inventors: Raymond Paul Beckett; Andrew Miller; Zoe Marie Spavold; Mark Whittaker, all of Oxford, United Kingdom

[73] Assignee: British Biotech Pharmaceuticals Limited, Oxford, United Kingdom

[21] Appl. No.: 08/930,620

[22] PCT Filed: Apr. 18, 1996

[86] PCT No.: PCT/GB96/00965

§ 371 Date: Oct. 7, 1997

§ 102(e) Date: Oct. 7, 1997

[87] PCT Pub. No.: WO96/33165

PCT Pub. Date: Oct. 24, 1996

[30] Foreign Application Priority Data

Apr. 18, 1995 [GB] United Kingdom .................... 9507799

[51] Int. Cl.$^6$ ..................................... A61K 31/44
[52] U.S. Cl. .......................... 514/332; 514/333; 514/558; 514/563; 514/575; 546/264; 546/285; 546/340; 546/341; 554/37; 562/426; 562/430; 562/441; 562/428; 562/623
[58] Field of Search ..................... 562/623, 441, 562/428, 430, 426; 546/264, 285, 340, 341; 554/37; 514/575, 563, 333, 558, 332

[56] References Cited

U.S. PATENT DOCUMENTS

| | | | |
|---|---|---|---|
| 5,643,964 | 7/1997 | Dickens | 514/575 |
| 5,652,262 | 7/1997 | Crimmin | 514/507 |
| 5,700,838 | 12/1997 | Dickens | 514/575 |
| 5,747,514 | 5/1998 | Beckett | 514/352 |

*Primary Examiner*—Michael L. Shippen
*Attorney, Agent, or Firm*—Banner & Witcoff

[57] ABSTRACT

Compounds of formula (I),

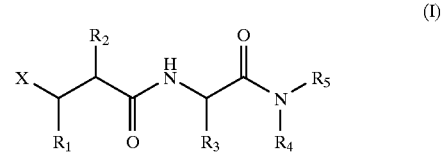

wherein X is a —$CO_2H$ or —CONHOH group; $R_4$ is a group —$CHR^xR^y$ wherein $R^x$ and $R^y$ independently represent optionally substituted phenyl or monocyclic heteroaryl rings, which optionally may be linked covalently to each other by a bond or by a $C_1$–$C_4$ alkylene or $C_2$–$C_4$ alkenylene bridge; and $R_1$, $R_2$, $R_3$ and $R_5$ are as defined in the specification are selective inhibitors of stromelysin-1 and matrilysin relative to human fibroblast collagenase and 72 KDa gelatinase.

17 Claims, No Drawings

DERIVATIVES OF SUCCINAMIDE AND THEIR USE AS METALLOPROTEINASE INHIBITOR

The present invention relates to therapeutically active hydroxamic acid and carboxylic acid derivatives, to processes for their preparation, to pharmaceutical compositions containing them, and to the use of such compounds in medicine. In particular, the compounds are inhibitors of metalloproteinases involved in tissue degradation. Some of the compounds of the invention are, in addition, inhibitors of the release of tumour necrosis factor from cells.

BACKGROUND TO THE INVENTION

Compounds which have the property of inhibiting the action of metalloproteinases involved in connective tissue breakdown such as collagenases, stromelysins and/or gelatinases (known as "matrix metalloproteinases", and herein referred to as MMPs) are thought to be potentially useful for the treatment or prophylaxis of conditions involving such tissue breakdown, for example rheumatoid arthritis, osteoarthritis, osteopenias such as osteoporosis, periodontitis, gingivitis, corneal epidermal or gastric ulceration, and tumour metastasis, invasion and growth. MMP inhibitors are also of potential value in the treatment of neuroinflammatory disorders, including those involving myelin degradation, for example multiple sclerosis, as well as in the management of angiogenesis dependent diseases, which include arthritic conditions and solid tumour growth as well as psoriasis, proliferative retinopathies, neovascular glaucoma, ocular tumours, angiofibromas and hemangiomas. However, the relative contributions of individual MMPs in any of the above disease states is not yet fully understood.

Metalloproteinases are characterised by the presence in the structure of a zinc(II) ionic site. It is now known that there exists a range of metalloproteinase enzymes that includes human fibroblast collagenase (Type 1), PMN-collagenase, 72 kDa-gelatinase, 92 kDa-gelatinase, stromelysin-1, stromelysin-2 and PUMP-1 (J. F. Woessner, FASEB J, 1991, 5, 2145–2154). Many known MMP inhibitors are peptide derivatives, based on naturally occuring amino acids, and are analogues of the cleavage site in the collagen molecule. A paper by Chapman et. al (J. Med. Chem. 1993, 36, 4293–4301) reports some general structure/activity findings in a series of N-carboxyalkyl peptides. Other known MMP inhibitors are less peptidic in structure, and may more properly be viewed as pseudopeptides or peptide mimetics. Such compounds usually have a functional group capable of binding to the zinc(II) site in the MMP, and known classes include those in which the zinc binding group is a hydroxamic acid, carboxylic acid, sulphydryl, and oxygenated phosphorus (eg phosphinic acid and phosphonamidate including aminophosphonic acid) groups.

Two known classes of pseudopeptide or peptide mimetic MMP inhibitors have a hydroxamic acid group and a carboxylic group respectively as their zinc binding groups. With a few exceptions, such known MMPs may be represented by the structural formula (I)

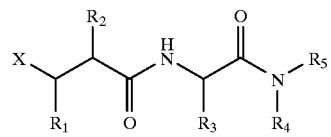

in which X is the zinc binding hydroxamic acid (—CONHOH) or carboxylic acid (—COOH) group and the groups $R_1$ to $R_5$ are variable in accordance with the specific prior art disclosures of such compounds. Examples of patent publications disclosing such structures are given below.

In such compounds, it is generally understood in the art that variation of the zinc binding group and the substituents $R_1$, $R_2$ and $R_3$ can have an appreciable effect on the relative inhibition of the metalloproteinase enzymes. The group X is thought to interact with metalloproteinase enzymes by binding to a zinc(II) ion in the active site. Generally the hydroxamic acid group is preferred over the carboxylic acid group in terms of inhibitory activity against the various metalloproteinase enzymes. However, the carboxylic acid group in combination with other substituents can provide selective inhibition of gelatinase (EP-489,577-A). The $R_1$, $R_2$ and $R_3$ groups are believed to occupy respectively the P1, P1' and P2' amino acid side chain binding sites for the natural enzyme substrate. There is evidence that a larger $R_1$ substituent can enhance activity against stromelysin, and that a $(C_1-C_6)$alkyl group (such as iso-butyl) at $R_2$ may be preferred for activity against collagenase whilst a phenylalkyl group (such as phenylpropyl) at $R_2$ may provide selectivity for gelatinase over the other metalloproteinases.

The precise role of each of the various types of MMP in mediating different clinical disease conditions is not understood at present. However, there is some evidence that for some clinical end points individual MMP types may have a greater causative role than others. For the treatment of conditions mediated mainly by one MMP type, clearly it would be desirable to use an MMP inhibitor which selectively inhibited that MMP, or at least was significantly more potent as an inhibitor of that MMP than of other MMP types.

Tumour necrosis factor (herein referred to as "TNF") is a cytokine which is produced initially as a cell-associated 28 kD precursor. It is released as an active, 17 kD form, which can mediate a large number of deleterious effects in vivo. When administered to animals or humans it causes inflammation, fever, cardiovascular effects, haemorrhage, coagulation and acute phase responses, similar to those seen during acute infections and shock states. Chronic administration can also cause cachexia and anorexia. Accumulation of excessive TNF can be lethal.

There is considerable evidence from animal model studies that blocking the effects of TNF with specific antibodies can be beneficial in acute infections, shock states, graft versus host reactions and autoimmune disease. TNF is also an autocrine growth factor for some myelomas and lymphomas and can act to inhibit normal haematopoiesis in patients with these tumours.

Compounds which inhibit the production or action of TNF are therefore thought to be potentially useful for the treatment or prophylaxis of many inflammatory, infectious, immunological or malignant diseases. These include, but are not restricted to, septic shock, haemodynamic shock and sepsis syndrome, post ischaemic reperfusion injury, malaria, Crohn's disease, mycobacterial infection, meningitis, psoriasis, congestive heart failure, fibrotic disease, cachexia, graft rejection, cancer, autoimmune disease, rheumatoid arthritis, multiple sclerosis, radiation damage, toxicity following administration of immunosuppressive monoclonal antibodies such as OKT3 or CAMPATH-1 and hyperoxic alveolar injury.

Since excessive TNF production has been noted in several diseases or conditions also characterised by MMP-mediated tissue degradation, compounds which inhibit both MMPs and TNF production may have particular advantages in the treatment or prophylaxis of diseases or conditions in which both mechanisms are involved.

As mentioned above, MMP inhibitors have been proposed with hydroxamic acid or carboxylic acid zinc binding groups. The following patent publications disclose hydroxamic acid-based and/or carboxylic acid-based MMP inhibitors:

U.S. Pat. No. 4,599,361 (Searle)
EP-A-0236872 (Roche)
EP-A-0274453 (Bellon)
WO 90/05716 (British Bio-technology)
WO 90/05719 (British Bio-technology)
WO 91/02716 (British Bio-technology)
EP-A-0489577 (Celltech)
EP-A-0489579 (Celltech)
EP-A-0497192 (Roche)
WO 92/13831 (British Bio-technology)
WO 92/17460 (SmithKline Beecham)
WO 92/22523 (Research Corporation Technologies)
WO 93/09090 (Yamanouchi)
WO 93/09097 (Sankyo)
WO 93/20047 (British Bio-technology)
WO 93/24449 (Celltech)
WO 93/24475 (Celltech)
EP-A-0574758 (Roche)
EP-A-0575844 (Roche)
WO 94/02446 (British Biotech)
WO 94/02447 (British Biotech)
WO 94/21612 (Otsuka)
WO 94/21625 (British Biotech)
WO 94/24140 (British Biotech)
WO 94/25434 (Celltech)
WO 94/25435 (Celltech)
WO 95/04033 (Celltech)
WO 95/04735 (Syntex)
WO 95/04715 (Kanebo)

BRIEF DESCRIPTION OF THE INVENTION

Pseudopeptide or peptide mimetic MMP inhibitors selectively active against stromelysins eg stromelysin-1, and against matrilysin, rather than collagenases eg human fibroblast collagenase, and gelatinases eg 72 KDa gelatinase, do not appear to form part of the art. Such compounds would have value in allowing more precisely directed treatment of diseases and conditions mediated primarily by stromelysin-1 and matrilysin, rather than collagenases and gelatinases.

This invention makes available a class of compounds of formula (I) above wherein X is a hydroxamic acid or carboxylic acid group characterised primarily in that the $R_4$ substituent is a group —$CHR^xR^y$ wherein $R^x$ and $R^y$ independently represent optionally substituted phenyl or monocyclic heteroaryl rings, which optionally may be linked covalently to each other by a bond or by a $C_1$–$C_4$ alkylene or $C_2$–$C_4$ alkenylene bridge. Such compounds are selective inhibitors of stromelysin-1 and matrilysin over human fibroblast collagenase, and 72 KDa gelatinase, ie are more active as inhibitors of stromelysin-1 than of human fibroblast collagenase, and 72 KDa gelatinase.

DETAILED DESCRIPTION OF THE INVENTION

The present invention provides compounds of general formula I

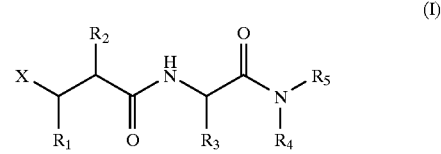

wherein
X is a —$CO_2H$ or —CONHOH group;
$R_1$ is ($C_1$–$C_6$)alkyl; ($C_2$–$C_6$)alkenyl; phenyl; substituted phenyl; phenyl ($C_1$–$C_6$)alkyl; substituted phenyl ($C_1$–$C_6$)alkyl; heterocyclyl; substituted heterocyclyl; heterocyclyl($C_1$–$C_6$)alkyl; substituted heterocyclyl ($C_1$–$C_6$)alkyl; a group $BSO_nA$- wherein n is 0, 1 or 2 and B is hydrogen or a ($C_1$–$C_6$)alkyl, phenyl, substituted phenyl, heterocyclyl, ($C_1$–$C_6$)acyl, phenacyl or substituted phenacyl group, and A represents ($C_1$–$C_6$) alkyl; amino; protected amino; acylamino; OH; SH; ($C_1$–$C_6$)alkoxy; ($C_1$–$C_6$)alkylamino; di-($C_1$–$C_6$) alkylamino; ($C_1$–$C_6$)alkylthio; aryl ($C_1$–$C_6$)alkyl; amino($C_1$–$C_6$)alkyl; hydroxy($C_1$–$C_6$)alkyl, mercapto ($C_1$–$C_6$)alkyl or carboxy($C_1$–$C_6$)alkyl wherein the amino-, hydroxy-, mercapto- or carboxyl-group are optionally protected or the carboxyl-group amidated; lower alkyl substituted by carbamoyl, mono(lower alkyl)carbamoyl, di(lower alkyl)carbamoyl, di(lower alkyl)amino, or carboxy-lower alkanoylamino,
$R_2$ is a ($C_1$–$C_6$)alkyl, ($C_2$–$C_6$)alkenyl, ($C_2$–$C_6$)alkynyl, phenyl($C_1$–$C_6$)alkyl, heteroaryl($C_1$–$C_6$)alkyl, cycloalkyl($C_1$–$C_6$)alkyl or cycloalkenyl($C_1$–$C_6$)alkyl group, any one of which may be optionally substituted by one or more substituents selected from ($C_1$–$C_6$) alkyl, —O($C_1$–$C_6$)alkyl, —$OCH_2Ph$ wherein the phenyl group may be optionally substituted, —S($C_1$–$C_6$) alkyl, halo and cyano (—CN);
$R_3$ is the characterising group of a natural or non-natural α amino acid in which any functional groups may be protected;
$R_4$ is a group —$CHR^xR^y$ wherein $R^x$ and $R^y$ independently represent optionally substituted phenyl or monocyclic heteroaryl rings, which optionally may be linked covalently to each other by a bond or by a $C_1$–$C_4$ alkylene or $C_2$–$C_4$ alkenylene bridge, either of which may be interrupted by an O or S atom;
$R_5$ is hydrogen or a ($C_1$–$C_6$)alkyl group;
or a salt, hydrate or solvate thereof.

As used herein the term "($C_1$–$C_6$)alkyl" or "lower alkyl" means a straight or branched chain alkyl moiety having from 1 to 6 carbon atoms, including for example, methyl, ethyl, n-propyl, isopropyl, n-butyl, isobutyl, sec-butyl, t-butyl, pentyl and hexyl.

The term "$C_1$–$C_4$ alkylene bridge" means one of the following divalent moieties, namely —$CH_2$—, —$CH_2CH_2$—, —$CH_2CH_2CH_2$—, or —$CH_2CH_2CH_2CH_2$—.

The term "($C_2$–$C_6$)alkenyl" means a straight or branched chain alkenyl moiety having from 2 to 6 carbon atoms having at least one double bond of either E or Z stereochemistry where applicable. This term would include, for example, vinyl, allyl, 1- and 2-butenyl and 2-methyl-2-propenyl.

The term "$C_2$–$C_4$ alkenylene bridge" means one of the following divalent moieties, namely —CH=CH—, —CH=CHCH$_2$—, —CH$_2$CH=CH— or —CH=CHCH$_2$CH$_2$—, CH$_2$CH=CHCH$_2$—, —CH$_2$CH$_2$CH=CH—, or —CH=CHCH=CH—.

The term "cycloalkyl" means a saturated alicyclic moiety having from 3–8 carbon atoms and includes, for example, cyclohexyl, cyclooctyl, cycloheptyl, cyclopentyl, cyclobutyl and cyclopropyl.

The term "cycloalkenyl" means an unsaturated alicyclic moiety having from 4–8 carbon atoms and includes, for example, cyclohexenyl, cyclooctenyl, cycloheptenyl, cyclopentenyl, and cyclobutenyl. In the case of cycloalkenyl rings of from 5–8 carbon atoms, the ring may contain more than one double bond.

The unqualified term "heterocyclyl" or "heterocyclic" means (i) a 5–7 membered heterocyclic ring containing one or more heteroatoms selected from S, N and O, and optionally fused to a benzene ring, including for example, pyrrolyl, furyl, thienyl, imidazolyl, oxazolyl, thiazolyl, thiadiazolyl, pyrazolyl, pyridinyl, pyrrolidinyl, pyrimidinyl, morpholinyl, piperazinyl, indolyl, benzimidazolyl, maleimido, succinimido, phthalimido, 1,2-dimethyl-3,5-dioxo-1,2,4-triazolidin-4-yl, 3,4,4-trimethyl-2,5-dioxo-1-imidazolidinyl, 2-methyl-3,5-dioxo-1,2,4-oxadiazol-4-yl, 3-methyl-2,4,5-trioxo-1-imidazolidinyl, 2,5-dioxo-3-phenyl-1-imidazolidinyl, 2-oxo-1-pyrrolidinyl, 2,5-dioxo-1-pyrrolidinyl or 2,6-dioxopiperidinyl, or (ii) a naphththalimido (ie 1,3-dihydro-1,3-dioxo-2H-benz[f]isoindol-2-yl), 1,3-dihydro-1-oxo-2H-benz[f]isoindol-2-yl, 1,3-dihydro-1,3-dioxo-2H-pyrrolo[3,4-b]quinolin-2-yl, or 2,3-dihydro-1,3-dioxo-1H-benz[d,e]isoquinolin-2-yl group.

The term "monocyclic heteroaryl" means a 5–7 membered substituted or unsubstituted aromatic heterocycle containing one or more heteroatoms. Illustrative of such rings are thienyl, furyl, pyrrolyl, imidazolyl, thiazolyl, pyrazolyl, isoxazolyl, isothiazolyl, trizolyl, thiadiazolyl, oxadiazolyl, pyridinyl, pyridazinyl, pyrimidinyl, pyrazinyl and triazinyl.

Unless otherwise specified in the context in which it occurs, the term "substituted" as applied to any moiety herein means substituted with up to four substituents, each of which independently may be ($C_1$–$C_6$)alkyl, ($C_1$–$C_6$)alkoxy, hydroxy, mercapto, ($C_1$–$C_6$)alkylthio, amino, halo (including fluoro, chloro, bromo and iodo), nitro, trifluoromethyl, —COOH, —CONH$_2$, —CN, —COOR$^A$ or —CONHR$^A$R$^A$ wherein R$^A$ is a ($C_1$–$C_6$)alkyl group or the residue of a natural alpha-amino acid.

The term "characterising group of a natural alpha-amino acid" means the characteristic side chain attached to the —CH(NH$_2$)(COOH) moiety in the following amino acids: glycine, alanine, valine, leucine, isoleucine, phenylalanine, tyrosine, tryptophan, serine, threonine, cysteine, methionine, asparagine, glutamine, lysine, histidine, arginine, glutamic acid and aspartic acid.

Natural alpha-amino acids which contain functional substituents, for example amino, carboxyl, hydroxy, mercapto, guanidyl, imidazolyl, or indolyl groups in their characteristic side chains include arginine, lysine, glutamic acid, aspartic acid, tryptophan, histidine, serine, threonine, tyrosine, and cysteine. When $R_3$ in the compounds of the invention is one of those side chains, the functional substituent may optionally be protected.

The term "protected" when used in relation to a functional substituent in a side chain of a natural alpha-amino acid means a derivative of such a substituent which is substantially non-functional. In this context, protected amino groups include amido and acylamino, protected hydroxy or mercapto groups include ethers and thioethers, protected carboxyl groups include esters, and imidazolyl, indolyl or guanidyl groups may be protected as t-butoxycarbonyl derivatives. These are only examples of the many protecting derivatives known in the art, and others will be known to the skilled man.

Salts of the compounds of the invention include physiologically acceptable acid addition salts for example hydrochlorides, hydrobromides, sulphates, methane sulphonates, p-toluenesulphonates, phosphates, acetates, citrates, succinates, lactates, tartrates, fumarates and maleates. Salts may also be formed with bases, for example sodium, potassium, magnesium, and calcium salts.

There are several chiral centres in the compounds according to the invention because of the presence of asymmetric carbon atoms. The presence of several asymmetric carbon atoms gives rise to a number of diastereomers with R or S stereochemistry at each chiral centre. General formula (I), and (unless specified otherwise) all other formulae in this specification are to be understood to include all such stereoisomers and mixtures (for example racemic mixtures) thereof.

In the compounds of the invention, the preferred stereochemistry is in general as follows:

C atom carrying the $R_1$ and X groups —S,
C atom carrying the $R_2$ group —R,
C atom carrying the $R_3$ group —S,
C atom carrying the $R^x$ and $R^y$ groups —R or S but mixtures in which the above configurations predominate are also contemplated.

As previously stated, the compounds of the invention are principally distinguished from the compounds disclosed in the prior art patent publications listed above by the identity of the group $R_4$. Accordingly, the groups $R_1$, $R_2$, $R_3$, and $R_5$ may be any of the groups which have been disclosed in the corresponding positions of compounds disclosed in any of those prior art patent publications listed above. Without limiting the generality of the foregoing, the following classes of substituent $R_3$ have been disclosed in the corresponding position of prior art compounds, and are therefore suitable $R_3$ groups for use in compounds of the present invention:

($C_1$–$C_6$)alkyl, benzyl, hydroxybenzyl, benzyloxybenzyl, ($C_1$–$C_6$)alkoxybenzyl, or benzyloxy($C_1$–$C_6$)alkyl group; and the characterising group of a natural α amino acid, in which any functional group may be protected, any amino group may be acylated and any carboxyl group present may be amidated; and a group -[Alk]$_n$R$_6$ where Alk is a ($C_1$–$C_6$)alkyl or ($C_2$–$C_6$) alkenyl group optionally interrupted by one or more —O—, or —S— atoms or —N(R$_7$)— groups [where R$_7$ is a hydrogen atom or a ($C_1$–$C_6$)alkyl group], n is 0 or 1, and R$_6$ is a optionally substituted cycloalkyl or cycloalkenyl group; or a benzyl group substituted in the phenyl ring by a group of formula —OCH$_2$COR$_8$ where R$_8$ is hydroxyl, amino, ($C_1$–$C_6$)alkoxy, phenyl($C_1$–$C_8$)alkoxy, ($C_1$–$C_6$) alkylamino, di(($C_1$–$C_6$)alkyl)amino, phenyl($C_1$–$C_6$) alkylamino, the residue of an amino acid or acid halide, ester or amide derivative thereof, said residue being linked via an amide bond, said amino acid being selected from glycine, α or β alanine, valine, leucine, isoleucine, phenylalanine, tyrosine, tryptophan, serine, threonine, cysteine, methionine, asparagine, glutamine, lysine, histidine, arginine, glutamic acid, and aspartic acid; or a heterocyclic(($C_1$–$C_6$)alkyl group, either being unsubstituted or mono- or di-substituted in the heterocyclic ring with halo, nitro, carboxy, ($C_1$–$C_6$)alkoxy, cyano, ($C_1$–$C_6$)alkanoyl, trifluoromethyl ($C_1$–$C_6$)alkyl, hydroxy, formyl, amino, ($C_1$–$C_6$)alkylamino, di($C_1$–$C_6$)alkylamino, mercapto, ($C_1$–$C_6$)alkylthio, hydroxy($C_1$–$C_6$)alkyl, mercapto($C_1$–$C_6$)alkyl or ($C_1$–$C_6$)alkylphenylmethyl.

$R_3$ may be a group $CR_a R_b R_c$ in which:

each of $R_a$, $R_b$ and $R_c$ is independently hydrogen, ($C_1$–$C_6$)alkyl, ($C_2$–$C_6$)alkenyl, ($C_2$–$C_6$)alkynyl, phenyl($C_1$–$C_6$)alkyl, ($C_3$–$C_8$)cycloalkyl, the foregoing being subject to the proviso that $R_a$, $R_b$ and $R_c$ are not all hydrogen; or $R_c$ is hydrogen, ($C_1$–$C_6$)alkyl, ($C_2$–$C_6$)alkenyl, ($C_2$–$C_6$)alkynyl, phenyl($C_1$–$C_6$)alkyl, or ($C_3$–$C_8$)cycloalkyl, and $R_a$ and $R_b$ together with the carbon atom to which they are attached form a 3 to 8 membered cycloalkyl or a 5- to 6-membered heterocyclic ring; or $R_a$, $R_b$ and $R_c$ together with the carbon atom to which they are attached form a tricyclic ring (for example adamantyl); or $R_a$ and $R_b$ are each independently ($C_1$–$C_6$)alkyl, ($C_2$–$C_6$)alkenyl, ($C_2$–$C_6$)alkynyl, phenyl($C_1$–$C_6$)alkyl, or a group as defined for $R_c$ below other than hydrogen, or $R_a$ and $R_b$ together with the carbon atom to which they are attached form a 3 to 8 membered cycloalkyl or a 3- to 8-membered heterocyclic ring, and $R_c$ is hydrogen, —OH, —SH, halogen, —CN, —$CO_2$H, ($C_1$–$C_4$) perfluoroalkyl, —$CH_2$OH, —$CO_2$($C_1$–$C_6$)alkyl, —O($C_1$–$C_6$)alkyl, —O($C_2$–$C_6$)alkenyl, —S($C_1$–$C_6$)alkyl, —SO($C_1$–$C_6$)alkyl, —$SO_2$($C_1$–$C_6$)alkyl, —S($C_2$–$C_6$)alkenyl, —SO($C_2$–$C_6$)alkenyl, —$SO_2$($C_2$–$C_6$)alkenyl or a group —Q—W wherein Q represents a bond or —O—, —S—, —SO— or —$SO_2$— and W represents a phenyl, phenylalkyl, ($C_3$–$C_8$)cycloalkyl, ($C_3$–$C_8$)cycloalkylalkyl, ($C_4$–$C_8$)cycloalkenyl, ($C_4$–$C_8$)cycloalkenylalkyl, heteroaryl or heteroarylalkyl group, which group W may optionally be substituted by one or more substituents independently selected from, hydroxyl, halogen, —CN, —$CO_2$H, —$CO_2$($C_1$–$C_6$)alkyl, —$CONH_2$, —CONH ($C_1$–$C_6$)alkyl, —CONH($C_1$–$C_6$alkyl)$_2$, —CHO, —$CH_2$OH, ($C_1$–$C_4$)perfluoroalkyl, —O($C_1$–$C_6$)alkyl, —S($C_1$–$C_6$)alkyl, —SO($C_1$–$C_6$)alkyl, —$SO_2$($C_1$–$C_6$) alkyl, —$NO_2$, —$NH_2$, —NH($C_1$–$C_6$)alkyl, —N(($C_1$–$C_6$)alkyl)$_2$, —NHCO($C_1$–$C_6$)alkyl, ($C_1$–$C_6$) alkyl, ($C_2$–$C_6$)alkenyl, ($C_2$–$C_6$)alkynyl, ($C_3$–$C_8$) cycloalkyl, ($C_4$–$C_8$)cycloalkenyl, phenyl or benzyl.

More specifically with respect to the groups $R_1$, $R_2$, $R_3$, $R_4$ and $R_5$ in compounds of the invention:

Examples of particular $R_1$ groups include methyl, ethyl, hydroxyl, methoxy allyl, thienylsulphanylmethyl, thienylsulphinylmethyl, thienylsulphonylmethyl and phthalimidomethyl. Presently preferred are compounds in which $R_1$ is hydroxyl, methoxy, allyl or phthalimidomethyl.

Examples of particular $R_2$ groups include iso-butyl, n-pentyl, n-hexyl, n-heptyl, n-octyl, n-nonyl, n-decyl, cyclohexylpropyl, phenylpropyl, phenylpropenyl, 4-chlorophenylpropyl, 4-methylphenylpropyl, 4-methoxyphenylpropyl, pyridine-4-ylpropyl, phenylbutyl, benzyloxybutyl, propyloxymethyl and propylsulphanyl. Presently preferred are compounds in which $R_2$ is isobutyl, n-octyl, n-decyl, phenylpropyl, or phenylpropenyl. Variation of the $R_2$ group may enhance the stromelysin-1 selectivity of a given compound relative not only to human fibroblast collagenase and 72 KDa gelatinase, but also relative to matrilysin. For example, groups $R_2$ with chain lengths in excess of the equivalent of about 7 carbon atoms, eg n-octyl or longer, may be preferred over shorter $R_2$ groups, eg isobutyl, for such stromelysin-1 selectivity.

Examples of particular $R_3$ groups include benzyl, isobutyl or t-butyl, 1-benzylthio-1-methylethyl, 1-hydroxy-1-methylethyl and 1-mercapto-1-methylethyl. Presently preferred are compounds in which $R_3$ is t-butyl, 1-hydroxy-1-methylethyl or 1-mercapto-1-methylethyl.

$R_4$ is a group —$CHR^x R^y$, and examples of $R^x$ and $R^y$ groups include optionally substituted phenyl, thienyl, furyl, pyrrolyl, imidazolyl, thiazolyl, pyrazolyl, isoxazolyl, isothiazolyl, trizolyl, thiadiazolyl, oxadiazolyl, pyridinyl, pyridazinyl, pyrimidinyl, pyrazinyl and triazinyl. Examples of particular $R^x$ and $R^y$ groups include phenyl, 2-fluorophenyl, 4-fluorophenyl, 2-pyridyl and 4-chlorophenyl. Also the $R^x$ and $R^y$ groups may be linked covalently to each other by a bond or by a $C_1$–$C_4$ alkylene or $C_2$–$C_4$ alkenylene bridge, and examples of such linked $R^x$ and $R^y$ groups include the case where $R_4$ is an optionally substituted 9-H-fluoren-9-yl group.

Examples of particular $R_5$ groups include hydrogen, methyl and ethyl. Presently preferred are compounds in which $R_5$ is hydrogen.

Specific examples of compounds of the present invention are:

$N^4$-[1S-(Benzhydryl-carbamoyl)-2,2-dimethyl-propyl]-2S, $N^1$-dihydroxy-3R-isobutyl-succinamide;

$N^4$-[1S-(9H-Fluoren-9-ylcarbamoyl)-2,2-dimethyl-propyl]-2S,$N^1$-dihydroxy-3R-isobutyl-succinamide;

$N^4$-(1S-{[(4-Chloro-phenyl)-phenyl-methyl]-carbamoyl}-2, 2-dimethyl-propyl)-2R,$N^1$-dihydroxy-3R-isobutyl-succinamide;

$N^4$-(1S-{[(4-Fluoro-phenyl)-phenyl-methyl]-carbamoyl}-2, 2-dimethyl-propyl)-2S,$N^1$-dihydroxy-3-isobutyl-succinamide;

$N^4$-(1S-{[(2-Fluoro-phenyl)-phenyl-methyl]-carbamoyl}-2, 2-dimethyl-propyl)-2S,$N^1$-dihydroxy-3R-isobutyl-succinamide;

$N^4$-[1S-(Benzhydryl-carbamoyl)-2-hydroxy-2-methyl-propyl]-2S,$N^1$-dihydroxy-3R-isobutyl-succinamide;

$N^4$-[1S-(Benzhydryl-carbamoyl)-2-hydroxy-2-methyl-propylcarbamoyl]-2S-methoxy-5R-methyl-hexanoic acid;

$N^4$-[1S-(Benzhydryl-carbamoyl)-2-hydroxy-2-methyl-propyl]-2S,$N^1$-dihydroxy-2-isobutyl-3R-methoxy-succinamide;

$N^4$-[1S-(Benzhydryl-carbamoyl)-2,2-dimethyl-propyl]-2S, $N^1$-dihydroxy-3R-(3-phenyl-ally)-succinamide;

$N^4$-[1S-(Benzhydryl-carbamoyl)-2,2-dimethyl-propyl]-2S, $N^1$-dihydroxy-3R-(3-phenyl-propyl)-succinamide;

$N^4$-{1S-[(Di-pyridin-2-yl-methyl)-carbamoyl]-2,2-dimethyl-propyl}-2S,$N^1$-dihydroxy-3R-isobutyl-succinamide;

2S-Allyl-$N^4$-[1S-(benzhydryl-carbamoyl)-2,2-dimethyl-propyl]-$N^1$-hydroxy-3R-isobutyl-succinamide; and 2S-Allyl-$N^4$-[1S-(benzhydryl-carbamoyl)-2,2-dimethyl-propyl]-$N^1$-hydroxy-3R-octyl-succinamide;
and salts, solvates or hydrates thereof.

Compounds according to the present invention in which X is a hydroxamic acid group —CONHOH may be prepared from corresponding compounds of the invention in which X is a carboxylic acid group —COOH or from the corresponding protected hydroxamic acid derivatives. That process, which forms another aspect of the invention, comprises:

(a) causing an acid of general formula (II)

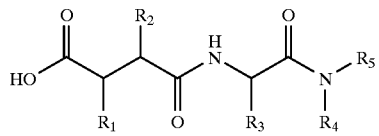

(II)

or an activated derivative thereof to react with hydroxylamine, O-protected hydroxylamine, or an N,O-diprotected hydroxylamine, or a salt thereof, $R_1$, $R_2$, $R_3$, $R_4$, and $R_5$ being as defined in general formula (I) except that any substituents in $R_1$, $R_2$, $R_3$, $R_4$, and $R_5$ which are potentially reactive with hydroxylamine, O-protected hydroxylamine, the N,O-diprotected hydroxylamine or their salts may themselves be protected from such reaction, then removing any protecting groups from the resultant hydroxamic acid moiety and from any protected substituents in $R_1$, $R_2$, $R_3$, $R_4$, and $R_5$ or (b) deprotecting a diprotected hydroxamic acid derivative of formula (IIb)

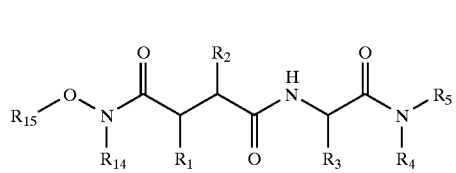

(IIb)

in which $R_1$, $R_2$, $R_3$, $R_4$, and $R_5$ are as defined in general formula (I), $R_{14}$ is an amino protecting group and $R_{15}$ is a hydroxyl protecting group.

For method (a) conversion of (II) to an activated derivative such as the pentafluorophenyl, hydroxysuccinyl, or hydroxybenzotriazolyl ester may be effected by reaction with the appropriate alcohol in the presence of a dehydrating agent such as dicyclohexyl dicarbodiimide (DCC), N,N-dimethylaminopropyl-N'-ethyl carbodiimide (EDC), or 2-ethoxy-1-ethoxycarbonyl-1,2-dihydroquinoline (EEDQ).

Protecting groups as referred to above are well known per se, for example from the techniques of peptide chemistry. Amino groups are often protectable by benzyloxycarbonyl, t-butoxycarbonyl or acetyl groups, or in the form of a phthalimido group. Hydroxy groups are often protectable as readily cleavable ethers such as the t-butyl or benzyl ether, or as readily cleavable esters such as the acetate. Carboxy groups are often protectable as readily cleavable esters, such as the t-butyl or benzyl ester.

Examples of O-protected hydroxylamines for use in method (a) above include O-benzylhydroxylamine, O-4-methoxybenzylhydroxylamine, O-trimethylsilylhydroxylamine, and O-tert-butoxycarbonylhydroxylamine.

Examples of N,O-diprotected hydroxylamines for use in method (a) above include N,O-bis(benzyl)hydroxylamine, N,O-bis(4-methoxybenzyl)hydroxylamine, N-tert-butoxycarbonyl-O-tert-butyldimethylsilylhydroxylamine, N-tert-butoxycarbonyl-O-tetrahydropyranylhydroxylamine, and N,O-bis(tert-butoxycarbonyl)hydroxylamine.

For method (b) suitable protecting groups $R_{14}$ and $R_{15}$ are benzyl and substituted benzyl (eg 4-methoxybenzyl). Such protecting groups may be removed by hydrogenolysis, while the 4-methoxybenzyl group may also be removed by acid hydrolysis.

In method (a) in the special case where $R_1$ in compound (I) is hydroxy, a particularly useful technique may be reaction of hydroxylamine with a dioxalone of formula (IIa):

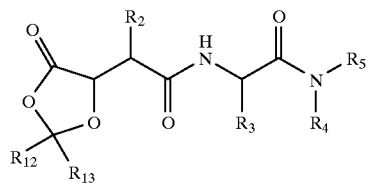

(IIa)

wherein the groups $R_{12}$ and $R_{13}$ are derived from a dioxalone forming reagent, and may be, for example, hydrogen, alkyl, phenyl or substituted phenyl. The dioxalone ring is opened on reaction with hydroxylamine to give the required hydroxamic acid derivative of formula (I).

Compounds according to the present invention in which X is a carboxylic acid group —COOH may be prepared by a process comprising: coupling an acid of formula (III) or an activated derivative thereof with an amine of formula (IV)

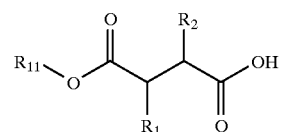

(III)

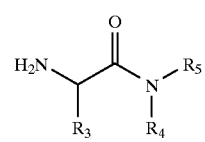

(IV)

wherein $R_1$ $R_2$, $R_3$, $R_4$, and $R_5$ are as defined in general formula (I) except that any substituents in $R_1$, $R_2$, $R_3$, $R_4$, and $R_5$ which are potentially reactive in the coupling reaction may themselves be protected from such reaction, and $R_{11}$ represents a hydroxy protecting group, and subsequently removing the protecting group $R_{11}$ and any protecting groups from $R_1$ $R_2$, $R_3$, $R_4$, and $R_5$.

Compounds of formula (IIb) may be prepared by a process comprising: causing an acid of formula (IIIa) or an activated derivative thereof to react with an amine of formula (IV)

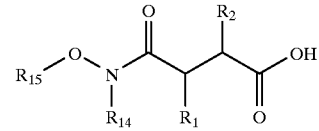

(IIIa)

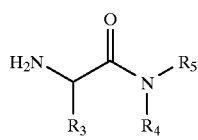

(IV)

wherein $R_1$, $R_2$, $R_3$, $R_4$, and $R_5$ are as defined in general formula (I) except that any substituents in $R_1$, $R_2$, $R_3$, $R_4$, and $R_5$ which are potentially reactive in the coupling reaction may themselves be protected from such reaction, $R_{14}$ is an amino protecting group and $R_{15}$ is a hydroxyl protecting group as referred to in connection with formula (IIb) above, and subsequently removing any protecting groups from $R_1$ $R_2$, $R_3$, $R_4$, and $R_5$.

Active derivatives of acids (III) and (IIIa) include activated esters such as the pentafluorophenyl ester, acid anhydrides and acid halides, eg chlorides. Suitable hydroxy protecting groups $R_{11}$ may be selected from those known in the art.

Amine intermediates of formula (IV) are either known compounds or may be prepared from known amino acid starting materials and amines of formula $HNR_4R_5$ using standard methods. Where these amines $HNR_4R_5$ are not commercially available, they may be prepared in two steps from the corresponding ketones (W. R. Roark et al, Bioorg. Med. Chem. 3, 29–39 (1995)).

In the special case where $R_1$ in compound (III) or (IIIa) is hydroxy, it too may be protected during the coupling of compounds (III) or (IIIa) and (IV). In the case where $R_1$ is hydroxy in compound (III) a particularly useful technique may be simultaneous protection of the two hydroxy groups as a dioxalone of formula (V):

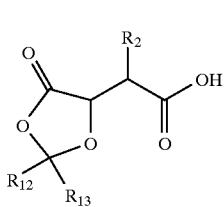

(V)

wherein the groups $R_{12}$ and $R_{13}$ are derived from a dioxalone forming reagent, and may be, for example, hydrogen, alkyl, phenyl or substituted phenyl.

As mentioned above, compounds of formula (I) are useful in human or veterinary medicine since they are active as inhibitors of MMPs, in particular stromelysin and matrilysin.

Accordingly in another aspect, this invention concerns a pharmaceutical or veterinary composition comprising a compound of formula (I) together with a pharmaceutically or veterinarily acceptable excipient or carrier. Included within this aspect of the invention is a pharmaceutical or veterinary composition comprising a compound of formula (I) together with a pharmaceutically or veterinarily acceptable excipient or carrier, characterised in that the composition is adapted for oral administration.

One or more compounds of general formula (I) may be present in the composition together with one or more excipient or carrier.

The compounds with which the invention is concerned may be prepared for administration by any route consistent with their pharmacokinetic properties. Orally administrable compositions may be in the form of tablets, capsules, powders, granules, ozenges, liquid or gel preparations, such as oral, topical, or sterile parenteral solutions or suspensions. Tablets and capsules for oral administration may be in unit dose presentation form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

The dosage unit involved in oral administration may contain from about 1 to 250 mg, eg from about 5 to 50 mg of a compound of the invention.

For topical application to the skin, the drug may be made up into a cream, lotion or ointment. Cream or ointment formulations which may be used for the drug are conventional formulations well known in the art, for example as described in standard textbooks of pharmaceutics such as the British Pharmacopoeia.

For topical application to the eye, the drug may be made up into a solution or suspension in a suitable sterile aqueous or non aqueous vehicle. Additives, for instance buffers such as sodium metabisulphite os disodium edeate; preservatives including bactericidal and fungicidal agents such as phenyl mercuric acetate or nitrate, benzalkonium chloride or chlorhexidine, and thickening agents such as hypromellose may also be included.

The dosage for topical administration will of course depend on the size of the area being treated. For the eyes, each dose may typically be in the range from 10 to 100 mg of the drug.

The active ingredient may also be administered parenterally in a sterile medium. Depending on the vehicle and concentration used, the drug can either be suspended or dissolved in the vehicle. Advantageously, adjuvants such as a local anaesthetic, preservative and buffering agents can be dissolved in the vehicle.

For use in the treatment of rheumatoid arthritis, the drug can be administered by the oral route or by injection intra-articularly into the affected joint.

The following Examples illustrate embodiments of the invention:

The amino acids used in the examples were commercially available or were prepared according to literature procedures.

The following abbreviations have been used throughout:
DMF N,N-Dimethylformamide
HOBt 1-Hydroxybenzotriazole
NMM N-Methylmorpholine TFA Trifluoroacetic acid
EDC N-Ethyl-N'-(3-dimethylaminopropyl)carbodiimide hydrochloride $^1$H and $^{13}$C NMR spectra were recorded using a Bruker AC 250E spectrometer at 250.1 and 62.9 MHz, respectively. Elemental microanalyses were performed by Medac Ltd. (Department of Chemistry, Brunel University, Uxbridge, Middlesex UB8 3PH).

EXAMPLE 1

$N^4$-[1S-(Benzhydryl-carbamoyl)-2,2-dimethyl-propyl]-2S,$N^1$-dihydroxy-3R-isobutyl-succinamide

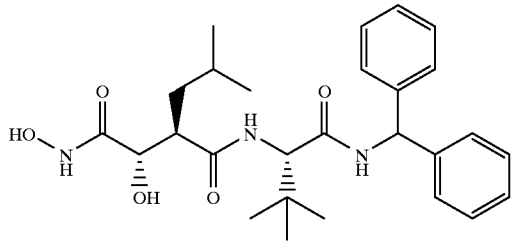

STEP A 2R-(2,2-Dimethyl-5-oxo-[1,3]dioxolan-4S-yl)-4-methyl-pentanoic acid[1S-(benzhydryl-carbamoyl)-2,2-dimethyl-propyl]-amide To an ice-cooled solution of L-tert-leucine-N-benzhydrylamide (5.10 g, 17.29 mmol) in DMF (30 ml), was added 2R-(2,2-Dimethyl-5-oxo-1-[1,3]dioxolan-4S-yl)-4-methyl-pentanoic acid 2,3,4,5,6-pentafluorophenyl ester (prepared according to WO 94/02447) (6.85 g, 17.29 mmol) in one portion. The reaction mixture was allowed to warm up to room temperature and was stirred overnight. The solvent was removed under pressure and the residue was dissolved in ethyl acetate (200 ml) and washed with 1M Na$_2$CO$_3$ (200 ml) and brine (200 ml). The organic phase was separated, dried over anhydrous MgSO$_4$, filtered and concentrated to a white foam. The product was obtained as a white solid (3.82 g, 50%) following recrystallisation from ethyl acetate-hexane. $^1$H-NMR; δ (CDCl$_3$), 7.37–7.18 (10H, m), 6.53 (1H, d, J=9.3 Hz), 6.47 (1H, d, J=7.7 Hz), 6.21 (1H, d, J=7.9 Hz), 4.39 (1H, d, J=5.9 Hz), 4.27 (1H, d, J=9.0 Hz), 2.72–2.66 (1H, m), 1.77–1.50 (9H, m), 1.01 (9H, s), 0.90 (3H, d, J=6.3 Hz) and 0.87 (3H, d, J=6.1 Hz).

STEP B $N^4$-[1S-(Benzhydryl-carbamoyl)-2,2-dimethyl-propyl]-2S,$N^1$-dihydroxy-3R-isobutyl-succinamide To a solution of hydroxylamine hydrochloride (2.61 g, 37.61 mmol) in methanol (50 ml), sodium methoxide (2.03 g, 37.61 mmol) was added. The reaction mixture was stirred for 2 hours at room temperature and then filtered to remove undissolved material. The filtrate was added to an ice-cooled solution of 2R-(2,2-dimethyl-5-oxo-[1,3]dioxolan-4S-yl)-4-methyl-pentanoic acid [1S-(benzhydryl-carbamoyl)-2,2-dimethyl-propyl]-amide in a mixture of DMF (10 ml) and methanol (30 ml). The reaction mixture was allowed to warm up to room temperature and was stirred overnight. The solvent was removed under reduced pressure and the residue were partitioned between ether (50 ml) and water (50 ml). The mixture was allowed to stand at room temperature overnight. The product was collected by filtration and washed with water and ether to leave a white crystalline solid (2.77 g, 76%). m.p. 200.5–201° C. $^1$H-NMR; δ(CD$_3$OD), 8.88 (1H, d, J=8.3 Hz), 7.84 (1H, d, J=9.3 Hz), 7.22 (10H, m), 6.16 (1H, m), 4.40 (1H, m), 3.95 (2H, d, J=6.9 Hz), 2.84 (1H, m), 1.63 (1H, m), 1.55 (1H, m), 1.13 (1H, m), 0.95 (9H, s) and 0.81 (6H, d, J=6.4 Hz). $^{13}$C-NMR; δ(CD$_3$OD), 175.6, 171.8, 171.6, 142.8, 129.6, 129.4, 129.1, 128.5, 128.2, 73.3, 62.0, 58.0, 49.5, 39.3, 35.8, 27.2, 27.0, 24.0 and 22.2. IR; ν$_{max}$ (KBr), 3366, 2943, 1643, 1519, 1378 and 700 cm$^{-1}$. Found: C 65.55, H 7.59, N 8.52%; C$_{27}$H$_{37}$N$_3$O$_5$. 0.6H$_2$O requires: C 65.59, H 7.79, N 8.50%.

The following additional compounds were prepared according to the methods of Example 1:

EXAMPLE 2

$N^4$-[1S-(9H-Fluoren-9-ylcarbamoyl)-2,2-dimethyl-propyl]-2S,$N^1$-dihydroxy-3R-isobutyl-succinamide

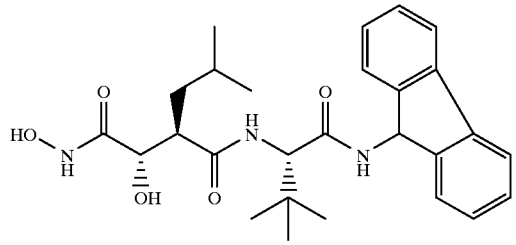

White solid. m.p. 209–211° $^1$H-NMR; δ(CD$_3$OD), 8.53 (1H, d, J=8.5 Hz), 7,96 (1H, d, J=9.3 Hz), 7.69 (2H, d, J=7.4 Hz), 7.43 (2H, d, J=7.3 Hz), 7.23 (4H, m), 6.04 (1H, d, J=8.2 Hz), 4.33 (1H, m), 4.00 (1H, d, J=6.8 Hz), 2.89 (1H, m), 1.59 (2H, m), 1.19 (1H, m), 1.05 (9H, s), 0.92 (3H, d, J=6.4 Hz) and 0.88 (3H, d, J=6.5 Hz). $^{13}$C-NMR; δ(CD$_3$OD), 175.5, 173.5, 171.6, 145.6, 145.3, 142.1, 141.9, 129.7, 128.7, 126.2, 126.0, 121.1, 121.0, 73.3, 62.3, 55.7, 49.5, 39.5, 35.5, 27.3, 27.1, 24.0 and 22.3. IR; ν$_{max}$ (KBr), 3305, 2858, 1651, 1520, 1369, 1069 and 737 cm$^{-1}$. Found C 66.14, H 7.20, N 8.45%; C$_{27}$H$_{35}$N$_3$O$_5$. 0.5 H$_2$O requires C 66.10, H 7.40, N 8.56%.

EXAMPLE 3

$N^4$-(1S-{[(4-Chloro-phenyl)-phenyl-methyl]-carbamoyl}-2,2-dimethyl-propyl)-2R,$N^1$-dihydroxy-3R-isobutyl-succinamide

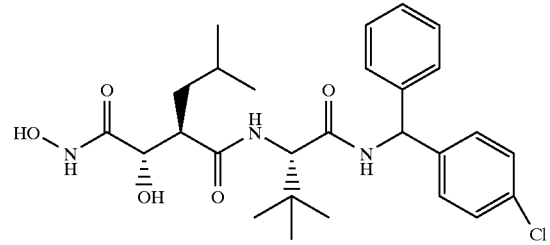

White powder. m.p. 192–194° C. $^1$H-NMR; δ(CD$_3$OD), 8.48 (1H, d, J=7.9 Hz), 7.21 (9H, m), 6.17 (1H, m), 4.00 (1H, d, J=5.7 Hz), 2.81 (1H, m), 1.59 (1H, m), 1.46 (1H, m), 1.24 (1H, m), 1.02 (1H, m), 0.95 (9H, s), 0.89 (3H, d, J=6.4 Hz), and 0.81 (3H, d, J=6.4 Hz). $^{13}$C-NMR; δ(CD$_3$OD), 175.6, 171.9, 171.6, 142.8, 129.6, 129.4, 129.1, 128.5 (2s), 128.2, 73.3, 61.9, 58.0, 49.5, 39.3, 35.7, 27.2, 27.0, 24.0 and 22.2. IR; ν$_{max}$ (KBr), 3300, 2942, 1637, 1519, 1367 and 697 cm$^{-1}$

EXAMPLE 4

N⁴-(1S-{[(4-Fluoro-phenyl)-phenyl-methyl]-carbamoyl}-2,2-dimethyl-propyl)-2S,N¹-dihydroxy-3-isobutyl-succinamide

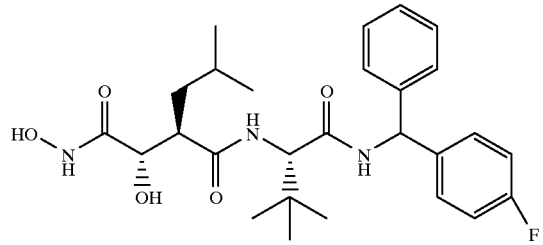

White solid (mixture of diastereomers). m.p. 118–125° C. ¹H-NMR; δ(CDCl₃): 9.68 (1H, br s), 8.05 (1H, br m), 7.27 (4H, m), 7.15 (3H, m), 6.99 (2H, t, J=8.6 Hz), 6.85 (1H, dd, J=7.6 Hz), 6.22 (1H, d, J=7.4 Hz), 5.30 (1H, br s), 4.31 (1H, d, J=9.3 Hz), 4.12 (1H, s), 3.32 (1H, br m), 1.75 (1H, m), 1.41 (2H, m), 0.92 (9H, s) and 0.84 (6H, dd, J=2.8 Hz). ¹³C-NMR; δ(CDCl₃): 174.9, 169.5, 168.5, 140.8, 140.6. 137.0, 129.3, 129.2, 128.9, 128.8, 128.7, 127.8, 127.6, 127.5, 127.1, 115.7, 115.5, 115.5, 115.3, 77.5, 73.1, 61.2, 56.5, 56.4, 44.7, 39.0, 34.9, 26.6, 25.9, 22.8 and 22.1. IR; $v_{max}$ (KBr) 3300, 2958, 2871, 1640, 1509, 1159, 1015 and 976 cm⁻¹.

EXAMPLE 5

N⁴-(1S-{[(2-Fluoro-phenyl)-phenyl-methyl]-carbamoyl}-2,2-dimethyl-propyl)-2S,N¹-dihydroxy-3R-isobutyl-succinamide

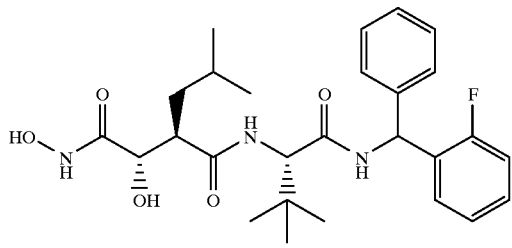

White solid (mixture of diastereomers). m.p. 150–151° C. ¹H-NMR; δ(CD₃OD): 8.81 (0.5H, d, J=8.3 Hz), 8.75 (0.5H, d, J=8.1 Hz), 7.79 (0.5H, d, J=9.2 Hz), 7.74 (0.5H, d, J=9.8 Hz), 7.27–6.91 (9H, m), 6.39 (0.5H, d, J=8.4 Hz), 6.31 (0.5H, d, J=8.1 Hz), 4.34 (0.5H, s), 4.30 (0.5H, s), 3.89 (0.5H, d, J=7.1 Hz), 3.85 (0.5H, d, J=7.4 Hz), 2.73 (1H, m), 1.55–1.02 (3H, m), 0.90 (4.5H, s), 0.87 (4.5H, s), 0.76 (3H, d, J=6.5 Hz), and 0.70 (3H, dd, J=3.9, 6.6 Hz). ¹³C-NMR; δ(CD₃OD): 175.5, 171.8, 171.7, 171.6, 162.8, 162.7, 160.9, 160.8, 141.6, 141.6, 130.6, 130.6, 130.5, 130.3, 130.3, 129.6, 129.5, 129.5, 128.6, 128.6, 128.4, 128.2, 125.3, 125.3, 125.3, 116.5, 116.4, 116.3, 116.2, 73.3, 73.2, 61.92, 61.8, 52.5, 52.4, 51.7, 51.6, 49.4, 39.3, 39.0, 35.6, 27.2, 27.1, 27.0, 26.9, 26.9, 24.0, 23.9, 22.2 and 22.0. Found: C 63.16, H 7.20, N 7.95%; C₂₇H₃₆FN₃O₅.0.7H₂O requires: C 63.07, H 7.33, N 8.17%.

EXAMPLE 6

N⁴-[1S-(Benzhydryl-carbamoyl)-2-hydroxy-2-methyl-propyl]-2S, N¹-dihydroxy-3R-isobutyl-succinamide

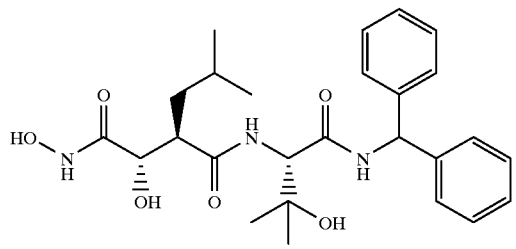

STEP A 2R,3-Dihydroxy-3-methyl-butyric acid ethyl ester

A suspension of Admixα (Trade Mark) (Aldrich, 90 g) in tert-butanol-water (1:1, 600 ml) was stirred vigorously at room temperature for 5 minutes. Methane sulphonamide (6 g, 63.08 mmol) was then added and the mixture cooled to 0° C. 3-Methyl-but-2-enoic acid ethyl ester (9.5 ml, 80.67 mmol) was added and stirring was continued at 0° C. for 9 hours then at room temperature overnight. Solid Na₂SO₃ (90 g) was added and stirring was continued for 1 hour. The reaction mixture was diluted with ethyl acetate (200 ml) and transfered to a separating funnel. The organic layer was removed and the aqueous phase extracted with ethyl acetate (3×100 ml). The combined organic layers were washed successively with 1N NaOH (200 ml) and brine (200 ml), dried over anhydrous MgSO₄, filtered and concentrated under reduced pressure. The crude product was purified by column chromatography (20% ethyl acetate in hexane) to give the title compound as a colourless oil (7.77 g, 60%). ¹H-NMR; δ(CDCl₃): 4.29 (2H, ddd, J=14.2, 7.2, 3.1 Hz), 3.95 (1H, d, J=6.8 Hz), 3.33 (1H, d, J=6.8 Hz), 2.76 (1H, s), 1.13 (3H, t, J=7.2 Hz), 1.29 (3H, s) and 1.21 (3H, s). IR; $v_{max}$(neat) 3439, 2980, 2938, 1731, 1372, 1270 and 1093. $[\alpha_D]^{20}$=−18.35 (c=2, CH₂Cl₂).

STEP B 5,5-Dimethyl-2,2-dioxo-[1,3,2]dioxathiolane-4R-carboxylic acid ethyl ester Thionyl chloride (3.4 ml, 46.66 mmol) was added dropwise to a solution of 2R-2,3-dihydroxy-3-methyl-butyric acid ethyl ester (6.3 g, 38.89 mmol) in carbon tetrachloride (50 ml) and the resulting solution was heated at reflux for 2 hours. The reaction mixture was cooled to 0° C. and acetonitrile (50 ml), RuCl₃.H₂O (7 mg), NaIO₄ (12.5 g, 58.32 mmol) and water (60 ml) were added. The resulting orange mixture was stirred at room temperature for 3 hours, poured into ether (120 ml) and the phases separated. The aqueous layer was extracted with ether (2×60 ml). The combined organic layers were washed successively with water (2×30 ml), saturated aqueous NaHCO₃ (30 ml) and brine (30 ml), dried over anhydrous MgSO₄, filtered and concentrated under reduced pressure to provide the title compound as a colourless oil (7.15 g, 82%). ¹H-NMR; δ(CDCl₃): 5.03 (1H, s) 4.34 (2H, dd, J=14.3, 7.0 Hz), 1.79 (3H, s), 1.57 (3H, s) and 1.35 (3H, t, J=7.0 Hz).

STEP C

2S-Azido-3-hydroxy-3-methyl-butyric acid ethyl ester

To a solution of 5,5-dimethyl-2,2-dioxo-[1,3,2] dioxathiolane-4R-carboxylic acid ethyl ester (2.0 g, 8.93 mmol) in (10:1) acetone:water (20 ml) was added $NaN_3$ (1.16 g, 18.75 mmol) and the mixture stirred vigorously at room temperature for 24 hours. Solvents were removed in vacuo and the residue treated with 20% aqueous $H_2SO_4$ (40 ml) and ether (40 ml) and viorously stirred at room temperature for a further 24 hours. The ether layer was separated and the aqueous phase extracted with ether (3×10 ml). The combined organic layers were dried over anhydrous $MgSO_4$, filtered and concentrated in vacuo. The crude product was purified by column chromatography (silica gel, 20% ethyl acetate in hexane) to provide the title compound as a colourless oil (1.0 g, 60%). $^1$H-NMR; $\delta(CDCl_3)$: 4.30 (2H, dd, J=14.3, 7.2 Hz), 3.78 (1H, s), 2.97 (1H, s), 1.34 (3H, t, J=7.3 Hz) and 1.29 (6H, s). IR; $v_{max}$(neat) 3534 (br), 2989, 2944, 2111, 1766, 1466, 1378, 1297 and 1058. $[\alpha_D]^{20}$=+ 20.55 (c=2, $CH_2Cl_2$).

STEP D

2S-Azido-3-hydroxy-3-methyl-butyric acid

To a solution of 2-azido-3-hydroxy-3-methyl-butyric acid ethyl ester (4.75 g, 25.40 mmol) in tetrahydrofuran at 0° C. was added a 1M aqueous solution of NaOH (26 ml, 26 mmol). The reaction mixture was stirred at 0° C. for 3 hours then diluted with ether (50 ml). The organic layer was separated and the aqueous phase extracted with ether (50 ml) then cooled to 0° C., acidified to pH 2 by dropwise addition of conc. HCl and extracted with ethyl acetate (5×100 ml). The combined organic extracts were dried over anhydrous $MgSO_4$, filtered and concentrated in vacuo to provide the title compound as a pale yellow oil (2.65 g, 66%). $^1$H-NMR; $\delta(CDCl_3)$: 6.76 (2H, br s), 3.92 (1H, s), 1.37 (3H, s) and 1.34 (3H, s). IR; $v_{max}(CCl_4)$, 3565 (br), 2978, 2120, 1737, 1719, 1548, 1243 and 1002. $[\alpha_D]^{20}$=+17.95 (c=2, $CH_2Cl_2$).

STEP E

2S-Azido-N-benzhydryl-3-hydroxy-3-methyl-butyramide

A solution of 2S-azido-3-hydroxy-3-methyl-butyric acid (1.3 g, 8.18 mmol) in DMF (30 ml) was cooled to 0° C. and treated with HOBt (1.32 g, 9.81 mmol) and EDC (1.88 g, 9.81 mmol). The reaction mixture was allowed to warm slowly to room temperature and stirred for three hours. C,C-Di-phenyl-methylamine (2.82 ml, 16.35 mmol) was added and the reaction mixture was stirred at room temperature overnight. Solvent was evaporated and the residue dissolved in dichloromethane (50 ml). The solution was washed successively with 1N aqueous HCl (2×30 ml), saturated aqueous $NaHCO_3$ (2×30 ml) and brine (30 ml), dried over anhydrous $MgSO_4$, filtered and concentrated to a yellow oil. The crude product was purified by column chromatography (silica gel, 40% ethyl acetate in hexane) to give the title compound as a colourless oil (1.86 g, 70%). $^1$H-NMR; $\delta(CDCl_3)$: 7.31 (11H, m), 6.24 (1H, d, J=8.2 Hz), 4.23 (1H, s), 3.89 (1H, s), 1.33 (3H, s) and 1.20 (3H, s).

STEP F

2S-Amino-N-benzhydryl-3-hydroxy-3-methyl-butyramide

To a solution of 2S-azido-N-benzhydryl-3-hydroxy-3-methyl-butyramide (1.86 g, 5.74 mmol) in methanol (20 ml) was added 20% $Pd(OH)_2$ on carbon (300 mg). The reaction mixture was vigorously stirred under an atmosphere of $H_2$ gas at room temperature and atmospheric pressure for 36 hours. The mixture was filtered through celite, washing well with methanol and the filtrate concentrated in vacuo to provide the title compound as an off-white solid (1.63 g, 96%). $^1$H-NMR; $\delta(CD_3OD)$: 7.21 (10H, m), 6.17 (1H, s), 3.71 (1H, s), 1.21 (3H, s) and 1.11 (3H, s).

The title compound was then prepared from 2S-amino-N-benzhydryl-3-hydroxy-3-methyl-butyramide by methods analogous to those described in Example 1:

$N^4$-[1S-(Benzhydryl-carbamoyl)-2-hydroxy-2-methyl-propyl]-2S,$N^1$-dihydroxy-3R-isobutyl-succinamide White solid. m.p. 201–202° C. $^1$H-NMR; $\delta(CD_3OD)$, 7.19 (10H, m), 6.09 (1H, s), 4.41 (1H, s), 3.87 (1H, d, J=7.2 Hz), 2.75 (1H, m), 1.52 (1H, m), 1.35 (1H, m), 1.13 (3H, s), 1.10 (3H, s), 1.06 (1H, m) and 0.73 (6H, dd, J=6.4, 2.1 Hz). $^{13}$C-NMR; $\delta(CD_3OD)$: 178.8, 174.0, 145.2, 145.1, 131.9, 131.8, 131.2, 130.9, 130.8, 130.7, 75.7, 75.3, 63.8, 60.6, 41.5, 30.1, 29.3, 28.8, 26.3 and 24.5. IR; $v_{max}$ (KBr) 3307, 2954, 1637, 1531, 1466, 1384, 1208, 1072 and 696 cm$^{-1}$.

EXAMPLE 7

$N^4$-[1S-(Benzhydryl-carbamoyl)-2-hydroxy-2-methyl-propylcarbamoyl]-2S-methoxy-5R-methyl-hexanoic acid

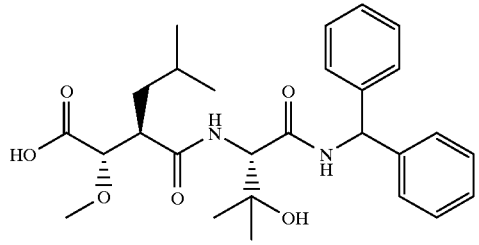

STEP A

2S-Hydroxy-3R-isobutyl-succinic acid dimethyl ester 2R-(2,2-Dimethyl-5-oxo-[1,3]-dioxalan-4S-yl)-4-methyl-pentanoic acid (75.0 g, 0.326 mol) was dissolved in methanol (500 ml) and cooled to 0° C. and the resulting solution was saturated with hydrogen chloride gas. The reaction mixture was allowed to warm to room temperature and stirred overnight. The solvent was removed under reduced pressure and the residue was dissolved in dichloromethane and washed successively with saturated $NaHCO_3$ and brine. The organic layer was dried (anhydrous $MgSO_4$), filtered and evaporated to dryness under reduced pressure to give the title compound (53 g, 9 75%). $^1$H-NMR; $\delta(CDCl_3)$, 4.10 (1H, d, J=4.0 Hz), 3.60 (3H, s), 3.50 (3H, s), 2.82–2.74 (1H, m), 1.61–1.40 (2H, m) 1.33–1.23 (1H, m) and 0.76–0.73 (6H, m).

STEP B 2R-isobutyl-3S-methoxy-succinic acid dimethyl ester

2S-Hydroxy-3R-isobutyl-succinic acid dimethyl ester (9.6 g 44 mmol) was dissolved in DMF (5 ml) and distilled iodomethane (3.3 ml) and silver (I) oxide (11.2 g) were added. The reaction was stirred with the exclusion of light for 5 days at room temperature. The solvent was removed under reduced pressure and the residue was purified by column chromatography (silica gel, dichloromethane) to give the title compound as a yellow viscous liquid, 4.7 g (46%). $^1$H-NMR; $\delta(CDCl_3)$, 3.83 (1H, d, J=7.5 Hz), 3.71 (3H, s), 3.62 (3H, s), 3.30 (3H, s), 2.89–2.80 (1H, m), 1.65–1.39 (2H, m), 1.15–1.04 (1H, m) and 0.83–0.81 (6H, m).

STEP C

2R-Isobutyl-3S-methoxy-succinic acid dilithium salt

Lithium hydroxide (1.76 g, 42.0 mmol) was added to a solution of 2R-isobutyl-3S-methoxy-succinic acid dimethyl ester (4.70 g, 20.0 mmol) in methanol (30 ml) and water (30 ml). The reaction mixture was stirred at room temperature for 2 hours then solvents were removed under reduced pressure to give the product as a yellow solid (4.40 g, 100%). $^1$H-NMR; $\delta$(CD$_3$OD), 3.52 (1H, d, J=5.1 Hz), 3.27 (3H, s), 2.69–2.61 (1H, m), 1.56–1.53 (2H, m), 1.34–1.28 (1H, m) and 0.82–0.78 (6H, m).

STEP D

2R-Isobutyl-3S-methoxy-succinic acid 4-methyl ester

2R-Isobutyl-3S-methoxy-succinic acid dilithium salt (4.40 g, 20.0 mmol) was dissolved in THF (30 ml), the solution was cooled to 0° C. and trifluoroacetic anhydride (30 ml) was added. The reaction was stirred for 4 hours, the solvent was removed under reduced pressure and the residue was dissolved in methanol (2 ml) at 0° C. and stirred to room temperature overnight. The solvent was removed under reduced pressure to give the title compound as a yellow oil (7.0 g, including residual salts), which was used without further purification in STEP E. $^1$H-NMR; $\delta$(CD$_3$OD), 7.61 (1H, d, J=7.5 Hz), 3.65 (3H, s), 3.24 (3H, s), 2.78–2.67 (1H, m), 1.56–1.42 (2H, m), 1.09–1.03 (1H, m) and 0.81–0.79 (6H, m).

STEP E

N$^4$-[1S-(Benzhydryl-carbamoyl)-2-hydroxy-2-methyl-propylcarbamoyl]-2S-methoxy-5R-methyl-hexanoic acid methyl ester A solution of 2-isobutyl-1-methoxy-succinic acid 1-methyl ester (0.33 g, 1.67 mmol) in DMF (10 ml) was cooled to 0° C. and treated with HOBt (0.27g, 2.01 mmol) and EDC (0.38 g, 2.01 mmol). The reaction mixture was allowed to warm slowly to room temperature and stirred for three hours. 2-Amino-N-benzhydryl-3-hydroxy-3-methyl-butyramide (0.5 g, 1.67 mmol) was added and the reaction mixture was stirred at 40° C. overnight. Solvent was evaporated and the residue dissolved in dichloromethane (25 ml). The solution was washed successively with 1N aqueous HCl (2×15 ml), saturated aqueous NaHCO$_3$ (2×15 ml) and brine (15 ml), dried over anhydrous MgSO$_4$, filtered and concentrated to a yellow gum. Trituration with ether provided the title compound as a white solid (220 mg, 27%). $^1$H-NMR; $\delta$(CDCl$_3$): 7.52 (1H, d, J=8.2 Hz), 7,26 (10H, m), 6.87 (1H, d, J=8.6 Hz), 6.25 (1H, d, J=7.9 Hz), 4.41 (1H, d, J=8.9 Hz), 3.82 (1H, d, J=6.1 Hz), 3.62 (3H, s) 3.30 (3H, s), 2.73 (1H, m), 1.62 (3H, m), 1.47 (1H, m), 1.29 (3H, s), 1.17 (3H, s) and 0.86 (6H, dd, J=6.5, 4.6 Hz).

STEP F

N$^4$-[1S-(Benzhydryl-carbamoyl)-2-hydroxy-2-methyl-propylcarbamoyl]-2S-methoxy-5R-methyl-hexanoic acid To a solution of N$^4$-[1S-(benzhydryl-carbamoyl)-2-hydroxy-2-methyl-propylcarbamoyl]-2S-methoxy-5R-methyl-hexanoic acid methyl ester (0.2 g, 0.418 mmol) in 3:2 tetrahydrofuran:water (5 ml) was added LiOH.H$_2$O (18.5 mg, 0.44 mmol) and the solution stirred at room temperature for 2 hours. The reaction mixture was then acidified to pH 1 with 1N aqueous HCl, and extracted with ethyl acetate (3×5 ml). The combined organic extracts were washed with brine, dried over anhydrous MgSO$_4$, filtered and concentrated in vacuo to provide the title compound as a white solid (180 mg, 93%). m.p. 118–119° C. $^1$H-NMR; $\delta$(CD$_3$OD): 8.60 (2H, d, J=8.2 Hz), 8.03 (1H, d, J=9.15 Hz), 7.19 (10H, m), 6.10 (1H, d, J=8.3 Hz), 4.42 (1H, d, J=9.1 Hz), 3.64 (1H, d, J=8.9 Hz), 2.71 (1H, m), 1.55 (1H, m), 1.29 (1H, m), 1.13 (3H, s), 1.11 (3H, s), 1.02 (1H, m), and 0.72 (6H, d, J=6.5 Hz). $^{13}$C-NMR; $\delta$(CD$_3$OD): 175.1, 174.6, 171.59, 142.7, 129.5, 129.5, 128.9, 128.4, 128.3, 128.3, 83.8, 72.9, 61.3, 58.5, 58.2, 48.9, 38.2, 27.6, 27.2, 26.1, 23.9 and 21.9.

EXAMPLE 8

N$^4$-[1S-(Benzhydryl-carbamoyl)-2-hydroxy-2-methyl-propyl]-2S,N$^1$-dihydroxy-2-isobutyl- 3R-methoxy-succinamide

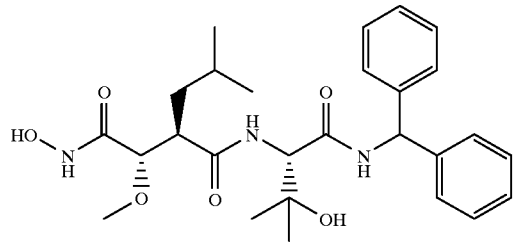

STEP A

N 1-[1-(Benzhydryl-carbamoyl)-2-hydroxy-2-methyl-propyl]-N 4-benzyloxy-2-isobutyl-3-methoxy-succinamide A solution of N 4-[1-(benzhydryl-carbamoyl)-2-hydroxy-2-methyl-propylcarbamoyl]-2-methoxy-5-methyl-hexanoic acid (160 mg, 0.33 mmol) in anhydrous tetrahydrofuran (5 ml) was cooled to –10° C. and treated with NMM (0.045 ml, 0.4 mmol) then isobutyl chloroformate (0.052 ml, 0.4 mmol), and the reaction mixture stirred at –10° C. for 20 minutes. O-Benzyl hydroxylamine (50 mg, 0.4 mmol) was added and stirring was continued at –10° C. for 2.5 hours. Solvent was removed in vacuo and trituration with ethyl acetate and hexane provided the title compound as a white solid (130 mg, 67%). $^1$H-NMR; $\delta$(CDCl$_3$): 8.20 (1H, d, J=8.1 Hz), 7.52 (1H, d, J=9.1 Hz), 7.31 (15H, m), 6.13 (1H, d, 8.1 Hz), 4.84 (2H, s), 4.49 (1H, d, J=9.1 Hz), 3.66 (1H, d, J=7.5 Hz), 3.11 (3H, s), 2.82 (2H, br m), 1.58 (1H, m), 1.36 (1H, m), 1.24 (1H, m), 1.20 (3H, s), 1.11 (3H, s) and 0.78 (6H, d, J=6.5 Hz).

STEP B

N$^4$-[1S-(Benzhydryl-carbamoyl)-2-hydroxy-2-methyl-propyl]-2,N$^1$-dihydroxy-2R-isobutyl-3S-methoxy-succinamide To a solution of N$^1$-[1S-(benzhydryl-carbamoyl)-2-hydroxy-2-methyl-propyl]-N$^4$-benzyloxy-2R-isobutyl-3S-methoxy-succinamide (130 mg, 0.22 mmol) in methanol (10 ml) was added 10% Pd on carbon (20 mg). The reaction mixture was vigorously stirred under an atmosphere of H$_2$ gas at room temperature and atmospheric pressure for 3 hours. The mixture was then filtered through celite, washing well with methanol and the filtrate concentrated in vacuo to provide the title compound as a pale yellow solid (80 mg, 73%). m.p.148.6–149° C. $^1$H-NMR; $\delta$(CD$_3$OD): 7.17 (10H, m), 6.08 (1H, s), 4.44 (1H, s), 3.45 (1H, d, J=9.5 Hz), 3.13

(3H, s), 2.70 (1H, m), 1.45 (1H, m), 1.32 (1H, m), 1.14 (3H, s), 1.10 (3H, s), 0.90 (1H, m) and 0.70 (6H, d, J=6.5 Hz). $^{13}$C-NMR; δ(CD$_3$OD): 175.2, 171.5, 169.3, 142.8, 129.5, 129.5, 128.9, 128.7, 128.5, 128.4, 128.3, 83.1, 72.9, 61.4, 58.2, 58.0, 48.9, 38.3, 27.8, 26.9, 26.1, 24.2 and 21.8.

EXAMPLE 9

N$^4$-[1S-(Benzhydryl-carbamoyl)-2,2-dimethyl-propyl]-2S,N$^1$-dihydroxy-3R-(3-phenyl-allyl)-succinamide

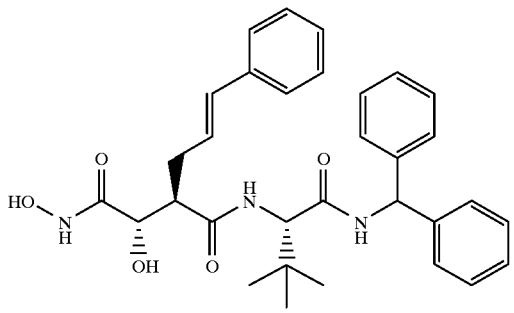

White solid (mixture of diastereomers). m.p. 97–99° C. $^1$H-NMR; δ(CD$_3$OD), 7.21–6.99 (15H, m), 6.36–6.30 (1H, m), 6.15–5.98 (2H, m), 4.38 (0.6H, s), 4.29 (0.4H, m), (0.4H, d, J=4.4 Hz), 4.12 (0.6H, d, J=6.1 Hz), 2.99–2.92 (1H, m), 2.54–2.32 (2H, m), 0.87 (6H, s) and 0.78 (3H, s). $^{13}$C-NMR; δ(CD$_3$OD), 175.0, 171.9, 171.5, 143.1, 138.8, 133.7, 129.5, 129.2,128.6, 128.5, 127.4, 72.7, 61.9, 58.2, 50.8, 35.8, 34.0, 31.6 and 27.4. IR; ν$_{max}$ (KBr), 3300, 2966, 1637, 1530, 1448, 1369, 1235, 1183, 1105, 1073, 1029, 966, 745, 698 cm$^{-1}$.

The starting material, 2R-(2,2-dimethyl-5-oxo-1-[1,3] dioxolan-4S-yl)-5-phenyl-hex-4-enoic acid 2,3,4,5,6-pentafluorophenyl ester, was prepared prepared by methods analogous to those described in WO 94/02447, substituting cinnamyl bromide for methallyl iodide.

EXAMPLE 10

N$^4$-[1S-(Benzhydryl-carbamoyl)-2,2-dimethyl-propyl]-2S,N$^1$-dihydroxy-3R-(3-phenyl-propyl)-succinamide

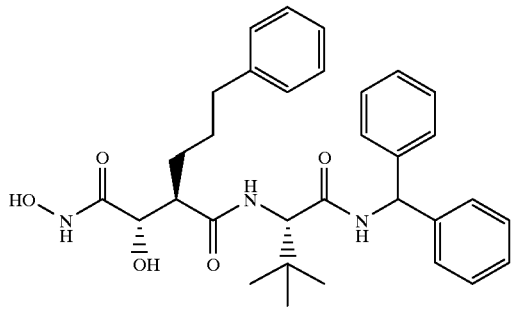

The title compound was prepared by analogy with Example 9. The cinnamyl sidechain was saturated by catalytic transfer hydrogenation (hydrogen gas, 10% palladium on charcoal in ethanol) at the penultimate step.

White solid (mixture of diastereomers). m.p. 86–88° C. $^1$H-NMR; δ(CD$_3$OD), 7.23–7.01 (15H, m), 6.10 (1H, d, J=3.7 Hz), 4.36 (0.6H, s), 4.29 (0.4H, s), 4.18 (0.4H, d, j=3.9 Hz), 3.95 (0.6H, d, J=6.9 Hz), 2.80–2.76 (1H, m), 2.51–2.39 (2H, m), 1.69–1.36 (4H, m) and 0.86 (9H, s). $^{13}$C-NMR; δ(CD$_3$OD), 175.5, 171.9, 171.5, 143.3, 142.7, 130.0, 129.5, 128.5, 128.2, 126.8, 73.2, 61.9, 58.1, 51.1, 50.1, 36.8, 35.7, 30.6, 30.1 and 27.3. IR; ν$_{max}$ (KBr), 3300, 2955, 1641, 1529,1496,1452, 1369,1234, 1077, 1029, 750 and 699 cm$^{-1}$.

EXAMPLE 11

N$^4$-{1S-[(Di-pyridin-2-yl-methyl)-carbamoyl]-2,2-dimethyl-propyl}-2S,N$^1$-dihydroxy-3R-isobutyl-succinamide

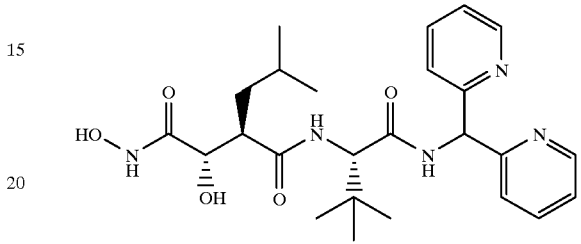

STEP A

C,C-Di-pyridin-2-yl-methylamine

To a solution of di-2-pyridyl ketone (1.84 g, 10 mmol) and ammonium acetate (7.7 g, 100 mmol) in anhydrous methanol (30 ml) was added sodium cyanoborohydride (1.26 g, 20 mmol) and the resulting solution heated at reflux for 5 hours. The reaction mixture was then cooled in an ice bath and acidified to pH 2 with concentrated HCl. Solvent was removed under reduced pressure and the residue dissolved in water (30 ml), washed with ether (3×10 ml) then basified to pH 10 with solid sodium hydroxide. The solution was then extracted with dichloromethane (3×20 ml) and the combined organic phase dried over anhydrous MgSO$_4$, filtered and concentrated to a brown oil (1.6 g, 86%). The crude product was used directly in the next step.

STEP B

N$_α$-2S-tert-Butoxycarbonylamino-N-(Di-pyridin-2-yl-methyl)-3,3-dimethyl-butyramide A solution of N$_α$-2-tert-butoxycarbonylamino-L-tert-leucine (1.98 g, 8.6 mmol) in DMF (15 ml) was cooled to 0° C. and treated with HOBt (1.39 g, 10.3 mmol) and EDC (1.98 g, 10.3 mmol). The reaction mixture was allowed to warm slowly to room temperature and stirred for three hours. A solution of C,C-di-pyridin-2-yl-methylamine (1.6 g, 8.6 mmol) was added and the reaction mixture stirred at room temperature overnight. Solvent was evaporated and the residue dissolved in dichloromethane (30 ml). The solution was washed with water (2×20 ml) and brine (20 ml). The organic phase was separated, dried over anhydrous MgSO$_4$, filtered and concentrated to a yellow oil. The crude product was purified by column chromatography (silica gel, 50% ethyl acetate in hexane) to give the title compound as a pale yellow solid (1.29 g, 38%). $^1$H-NMR; δ(CDCl$_3$): 8.55 (2H, m), 8.15 (1H, d, J=6.3 Hz), 7.61 (2H, m), 7.45 (1H, d, J=7.5 Hz), 7.38 (1H, d, J=7.6 Hz), 7.15 (2H, m), 6.19 (1H, d, J=6.4 Hz), 5.29 (1H, J=9.2 Hz), 4.07 (1H, d, J=9.2 Hz), 1.43 (9H, s) and 0.99 (9H, s).

STEP C

N$_α$-2S-Amino-N-(di-pyridin-2-yl-methyl)-3,3-dimethyl-butyramide

N$_α$-2S-tert-Butoxycarbonylamino-N-(di-pyridin-2-yl-methyl)-3,3-dimethyl-butyramide (1.29 g, 3.24 mmol) was dissolved in methanol (5 ml) and added to a cooled, 2M solution of hydrochloric acid in ethyl acetate (25 ml). The reaction mixture was allowed to warm to room temperature and was stirred overnight. The solvent was evaporated under reduced pressure and the residue dissolved in methanol (15 ml) and water (5 ml). Amberlite OH— resin was added until the solution reached pH 8. The resin was removed by filtration, washed well with methanol, and the combined filtrates concentrated at reduced pressure to provide the title compound as a yellow solid (1.10 g, 100%). $^1$H-NMR; $\delta$(CDCl$_3$): 8.68 (1H, d, J=6.3 Hz), 8.53 (2H, m), 7.63 (2H, m), 7.41 (2H, dd, J=16.7, 8.7 Hz), 7.14 (2H, m), 6.24 (1H, d, J=6.6 Hz), 3.45 (1H, d, J=11.1 Hz), 3.20 (2H, br s) and 1.01 (9H, s).

The title compound was then prepared by methods analogous to those described in Example 1:

N$^4$-{1S-[(Di-pyridin-2-yl-methyl)-carbamoyl]-2,2-dimethyl-propyl}-2S,N$^1$-dihydroxy-3R-isobutyl-succinamide White solid. m.p. 98–106° C. $^1$H-NMR; $\delta$(CD$_3$OD) 8.39 (2H, dd, J=2.2 Hz), 7.69 (2H, dd, J=7.7 Hz), 7.38 (2H, d, J=7.8 Hz), 7.20 (2H, dd, J=6.4, 5.0 Hz), 6.18 (1H, s), 4.32 (1H, s), 3.95 (1H, d, J=6.2 Hz), 2.79 (1H, m), 1.53 (1H, m), 1.41 (1H, m), 1.14 (1H, m), 0.90 (9H, s) and 0.73 (6H, dd, J=7.3 Hz). $^{13}$C-NMR; $\delta$(CD$_3$OD): 175.8, 172.3, 171.5, 160.0, 159.8, 150.0, 149.7, 139.1, 138.9, 124.2, 124.0, 123.7, 73.1, 62.4, 60.7, 39.5, 35.4, 27.2, 26.9, 23.8 and 22.3. IR; $v_{max}$ (KBr) 3318, 2962, 1653, 1593, 1522, 1368, 1096, 1015 and 754 cm$^{-1}$.

EXAMPLE 12

2S-Allyl-N$^4$-[1S-(benzhydryl-carbamoyl)-2,2-dimethyl-propyl]-N$^1$-hydroxy-3R-isobutyl-succinamide

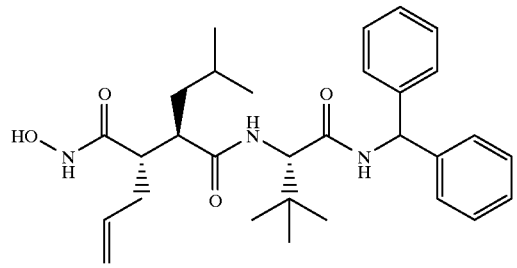

STEP A

2R,S-{1R-[1S-(Benzhydryl-carbamoyl)-2,2-dimethyl-propylcarbamoyl]-3-methylbutyl}-pent-4-enoic acid tert-butyl ester 2R,S-Allyl-3R-isobutyl-succinic acid 4-tert-butyl ester (mixture of diastereoisomers, 3:1, SR:RR; prepared according to WO 94/21625) (1.82 g, 6.76 mmol) was dissolved in DMF (80 ml) and cooled to 0° C., during the addition of HOBt (1.09 g, 8.11 mmol) and EDC (1.60 g, 8.11 mmol). The reaction mixture was stirred at room temperature for 5 hours and L-tert-leucine-N-benzhydrylamide (2.00 g, 6.76 mmol) was added. The reaction mixture was stirred overnight. The solvent was removed under reduced pressure and the residue was dissolved in ethyl acetate (150 ml) and washed with 1N HCl (100 ml) and 1M Na$_2$CO$_3$ (100 ml). The organic phase was separated, dried over anhydrous MgSO$_4$, filtered and concentrated to a yellow oil. The crude product was purified by column chromatography (silica gel, 20% ethyl acetate in hexane) to give the title compound as a white foam (1.91 g, 52%; mixture of diastereoisomers, 5:1, SRS:RRS). $^1$H-NMR; $\delta$(CDCl$_3$, major diastereoisomer), 7.35–7.15 (11H, m), 6.37–6.21 (2H, m), 5.73–5.67 (1H, m), 5.06–4.99 (1H, m), 4.28 (1H, d, J=9.2 Hz), 2.59–2.22 (4H, br m), 1.62–1.59 (1H, m), 1.44 (9H, s), 1.40–1.22 (1H, m), 1.20–1.00 (1H, m), 1.01 (9H, s), 0.83 (3H, d, J=7.6 Hz) and 0.80 (3H, d, J=6.5 Hz).

STEP B

2S-{1R-[1S-(Benzhydryl-carbamoyl)-2,2-dimethyl-propylcarbamoyl]-3-methylbutyl}-pent-4-enoic acid 2R,S-{1R-[1S-(Benzhydryl-carbamoyl)-2,2-dimethyl-propylcarbamoyl]-3-methylbutyl}-pent-4-enoic acid tert-butyl ester (5:1, SRS:RRS from above) (1.91 g, 3.48 mmol) was dissolved in dichloromethane (6 ml) and TFA (6 ml) and the reaction mixture was stored at 4° C. overnight. The solvent was removed under reduced pressure and the residue was azeotroped with toluene (5×50 ml). The crude product was recrystallised from ethyl acetate to give the title compound as a white crystalline solid (1.20 g, 71%; single diastereoisomer). $^1$H-NMR; $\delta$(CD$_3$OD), 8.84 (1H, d, J=8.5 Hz), 7.92 (1H, d, J=9.1 Hz), 7.25–7.08 (10H, m), 6.10 (1H, d, J=8.5 Hz), 5.73–5.56 (1H, m), 4.96–4.86 (2H, m), 4.37 (1H, d, J=9.4 Hz), 3.21–3.19 (1H, m), 2.56–2.45 (1H, m), 2.19–2.14 (2H, m), 1.62–1.48 (1H, m), 1.30–1.15 (1H, m), 1.10–10.87 (1H, m), 0.88 (9H, s), 0.81 (3H, d, J=6.8 Hz) and 0.78 (3H, d, J=7.0 Hz).

STEP C

2S-Allyl-N$^4$-[1S-(benzhydryl-carbamoyl)-2,2-dimethyl-propyl]-N$^1$-hydroxy-3R-isobutyl-succinamide To a solution of 2S-{1R-[1S-(benzhydryl-carbamoyl)-2,2-dimethyl-propylcarbamoyl]-3-methylbutyl}-pent-4-enoic acid (1.20 g, 2.44 mmol) in DMF (100 ml), HOBt (0.39 g, 2.93 mmol) and EDC (0.58 g, 2.93 mmol) were added. The reaction mixture was stirred for 6 hours at room temperature before hydroxylamine hydrochloride (0.25 g, 3.66 mmol) and NMM (0.40 ml, 3.66 mmol) were added. The reaction mixture was stirred for 2 days. The solvent was removed and the residue was suspended between ether (50 ml) and water (50 ml) for 3 hours. The product was filtered, suspended in ethyl acetate (100 ml) and refluxed for a few minutes. The product was filtered and dried to leave a white crystalline solid (1.082 g, 87%). m.p. 220.5–221° C. $^1$H-NMR; $\delta$(CD$_3$OD), 8.83 (1H, d, J=8.4 Hz), 8.02 (1H, d, J=9.5 Hz), 7.21–7.08 (10H, br m), 6.08 (1H, d, J=8.6 Hz), 5.61–5.48 (1H, br m), 4.92–4.85 (2H, m), 4.37 (1H, d, J=9.3 Hz), 2.62–2.55 (1H, m), 2.28–1.98 (3H, m), 1.47–1.36 (1H, m), 1.30–1.17 (1H, m), 1.02–0.91 (10H, m), 0.67 (3H, d, J=6.3 Hz) and 0.65 (3H, d, J=6.4 Hz). $^{13}$C-NMR; $\delta$(CD$_3$OD), 176.5, 172.4, 171.7, 143.0, 142.9, 136.0, 129.6, 129.4, 129.1, 128.5, 128.2, 117.5, 62.3, 58.0, 48.1, 41.8, 36.4, 35.5, 27.4, 27.0, 24.7, 21.7 and 14.5. IR; $v_{max}$ (KBr), 3295, 2954, 1637, 1525 and 699 cm$^{-1}$.

The following additional compound was prepared according to the methods of Example 12. The starting material 2R,S-Allyl-3R-octyl-succinic acid 4-tert-butyl ester was prepared by methods analogous to those described in WO 94/21625, substituting n-decanoyl chloride for 4-methyl-pentanoyl chloride.

EXAMPLE 13

2S-Allyl-$N^4$-[1S-(benzhydryl-carbamoyl)-2,2-dimethyl-propyl]-$N^1$-hydroxy-3R-octyl-succinamide

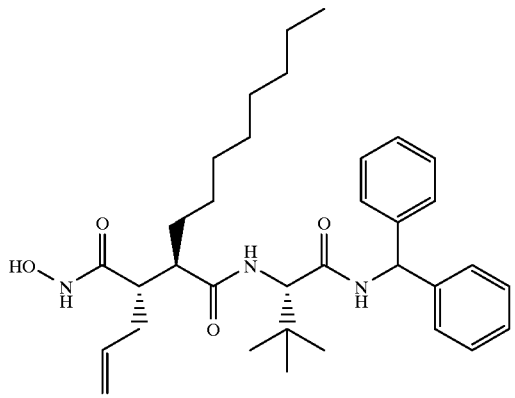

White solid. m.p. 219–219.5° C. $^1$H-NMR; δ(CD$_3$OD), 8.84 (1H, d, J=8.6 Hz), 8.04 (1H, d, J=9.3 Hz), 7.26–7.08 (10H, br m), 6.10 (1H, d, J=8.6 Hz), 5.65–5.48 (1H, m), 4.93–4.85 (2H, m), 4.38 (1H, d, J=9.4 Hz), 2.59–2.48 (1H, m), 2.24–2.13 (2H, m), 2.07–1.97 (1H, m), 1.37–0.99 (14H, br m), 0.89 (9H, s) and 0.78 (3H, t, J=6.5 Hz). $^{13}$C-NMR; δ(CD$_3$OD), 176.6, 172.4, 171.7, 171.6, 143.0, 142.8, 136.01 129.5, 129.4, 129.1, 128.5, 128.4, 128.1, 117.5, 62.0, 58.0, 57.9, 49.8, 47.6, 36.4, 35.4, 33.0, 32.6, 30.8, 30.4, 28.2, 27.3, 23.7 and 14.5. IR; $v_{max}$(KBr), 3295, 2931, 1637, 1525, 1372 and 697 cm$^{-1}$. Found: C 70.47, H 8.67, N 7.54%; C$_{34}$H$_{49}$N$_3$O$_4$. 0.9H$_2$O requires C 70.41, H 8.83, N 7.24%.

BIOLOGICAL EXAMPLE

The following table compares the in vitro potencies of compounds of the present invention against stromelysin-1, matrilysin, 72 KDa gelatinase and human fibroblast collagenase. Data for two compounds known in the art where R$_4$=CH$_3$ (Comparators 1 and 2) are included.

Comparator 1: 2S,$N^1$-Dihydroxy-$N^4$-(2,2-dimethyl-1S-methylcarbamoyl-propyl)-3R-isobutyl-succinamide.

Comparator 2: 2S-Allyl-$N^4$-(2,2-dimethyl-1S-methylcarbamoyl-propyl)-$N^1$-hydroxy-3R-isobutyl-succinamide.

The potency of compounds of the present invention as inhibitors of human fibroblast collagenase was determined by the procedure of Cawston and Barrett, (Anal. Biochem., 99, 340–345, 1979), hereby incorporated by reference, whereby a 1 mM solution of the compound being tested, or a dilution thereof, was incubated at 37° C. for 16 hours with collagen and collagenase (buffered with 25 mM Hepes, pH 7.5 containing 5 mM CaCl$_2$, 0.05% Brij 35 and 0.02% NaN$_3$). The collagen was acetylated $^{14}$C collagen prepared by the method of Cawston and Murphy, (Methods in Enzymology, 80, 711, 1981), hereby incorporated by reference. The samples were centrifuged to sediment undigested collagen, and an aliquot of the radioactive supernatant removed for assay on a scintillation counter as a measure of hydrolysis. The collagenase activity in the presence of 1 mM of the test compound, or a dilution thereof, was compared to activity in a control devoid of inhibitor and the result reported below as that of inhibitor concentration effecting 50% inhibition of the collagenase activity (IC$_{50}$).

The potency of compounds of the invention as inhibitors of stromelysin-1 was determined by the procedure of Cawston et al, (Biochem. J, 195, 159–165, 1981), hereby incorporated by reference, whereby a 1 mM solution of the compound being tested, or a dilution thereof, was incubated at 37° C. for 16 hours with stromelysin and $^{14}$C acetylate casein (buffered with 25 mM Hepes, pH 7.5 containing 5 mM CaCl$_2$, 0.05% Brij 35 and 0.02% NaN$_3$). The casein was acetylated $^{14}$C casein prepared by the method of Cawston et al. (ibid.). The stromelysin activity in the presence of 1 mM of the test compound, or a dilution thereof, was compared to activity in a control devoid of inhibitor and the result reported below as that of inhibitor concentration effecting 50% inhibition of the stromelysin activity (IC$_{50}$).

The potency of compounds of the invention as inhibitors of 72 kDa gelatinase was determined by a procedure based on the method of Sellers et al., Biochem. J., 171, 493–496 (1979). 72 kDa gelatinase, derived from RPMI-7951 cells was purified by gelatin-agarose chromatography. The enzyme was activated by incubation with aminophenyl mercuric acetate and approximately 0.05 units was incubated with 50 μg [$^{14}$C]-radiolabelled gelatin in an appropriate buffer for 16 hours at 37° C. At the end of the incubation 50 μg bovine serum albumin, together with trichloroacetic acid (final concentration 16%) were added to stop the reaction and to precipitate any undegraded substrate. The reaction tubes were placed on ice for 15 minutes before centrifugation at 10,000 g for 15 minutes to sediment the precipitated substrate. A 200 μl aliquot of the reaction supernatant was removed and the radioactivity determined by liquid scintillation counting. The effect of the inhibitors was determined by reference to a dose response curve. The IC50 (the concentration of inhibitor required to cause a 50% decrease in enzyme activity) was obtained by fitting a curve to the data and computing the concentration of inhibitor required to achieve 50% inhibition of the enzyme. For each IC50 determination, the effect on gelatinase activity of at least 8 concentrations of the inhibitor were examined. The inhibitors were dissolved DMSO and diluted to the appropriate test concentrations.

The potency of the compounds of the invention as inhibitors of recombinant matrilysin (PUMP-1) was determined using an assay which was adapted from the assay used to measure the stromelysin activity. A solution of the compound being tested, dissolved in dimethyl sulphoxide (DMSO) was incubated at 37° C. for 16 hours with matrilysin and $^{14}$C-acetylated casein (buffered with 50 mM Tris HCl, pH 7.6 containing 5 mM CaCl$_2$, 0.05% (v/v) Brij 35). The reaction was terminated by the addition of trichloroacetic acid (TCA), and the substrate separated from soluble degradation products by centrifugation. The radioactivity associated with the TCA-soluble products released from casein by matrilysin was determined by liquid scintillation counting. The effect of BB-2516 was deterined by examining a dose-response curve. The concentration of inhibitor required to cause a 50% decrease in enzyme activity (IC$_{50}$) was obtained by manual interpolation from the graph.

| | In vitro inhibitory activity IC$_{50}$ (nM) | | | |
|---|---|---|---|---|
| Test Compound | Fib. Collag. (MMP-1) | Gelatinase A (MMP-2) | Stromelysin-1 (MMP-3) | Matrilysin (MMP-7) |
| Comparator 1 | 5 | 6 | 200 | 20 |
| Example 1 | 600 | 3000 | 50 | 4 |
| Example 2 | 2000 | 17000 | 200 | 70 |
| Example 3 | 400 | 2000 | 200 | 10 |
| Example 4 | 400 | 500 | 60 | 9 |
| Example 5 | 700 | 600 | 100 | 9 |
| Example 6 | 2000 | 600 | 200 | 15 |
| Example 7 | 40% I @ 100 µM | 50% I @ 100 µM | 20000 | NT |
| Example 8 | 700 | 1000 | 20 | 9 |
| Example 9 | 30% I @ 100 µM | 40000 | 800 | 500 |
| Example 10 | 10000 | 8000 | 90 | 1000 |
| Example 11 | 300 | 1000 | 200 | 20 |
| Comparator 2 | 4 | 15 | 80 | 20 |
| Example 12 | 800 | 40000 | 80 | 30 |
| Example 13 | 30000 | 20000 | 60 | 400 |

We claim:

1. A compound of formula I

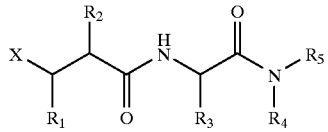

(I)

wherein

X is a —CO$_2$H or —CONHOH group;

R$_1$ is (C$_1$–C$_6$)alkyl; (C$_2$–C$_6$)alkenyl; phenyl; substituted phenyl; phenyl (C$_1$–C$_6$)alkyl); substituted phenyl (C$_1$–C$_6$)alkyl; heterocyclyl; substituted heterocyclyl; heterocyclyl(C$_1$–C$_6$)alkyl; substituted heterocyclyl (C$_1$–C$_6$)alkyl; a group BSO$_n$A— wherein n is 0, 1 or 2 and B is hydrogen or a (C$_1$–C$_6$)alkyl, phenyl, substituted phenyl, heterocyclyl, (C$_1$–C$_6$)acyl, phenacyl or substituted phenacyl group, and A represents (C$_1$–C$_6$) alkyl; amino; protected amino; acylamino; OH; SH; (C$_1$–C$_6$)alkoxy; (C$_1$–C$_6$)alkylamino; di-(C$_1$–C$_6$) alkylamino; (C$_1$–C$_6$)alkylthio; aryl(C$_1$–C$_6$)alkyl; amino(C$_1$–C$_6$)alkyl; hydroxy(C$_1$–C$_6$)alkyl, mercapto (C$_1$–C$_6$)alkyl or carboxy(C$_1$–C$_6$)alkyl wherein the amino-, hydroxy-, mercapto- or carboxyl-group are optionally protected or the carboxyl-group amidated; lower alkyl substituted by carbamoyl, mono(lower alkyl)carbamoyl, di(lower alkyl)carbamoyl, di(lower alkyl)amino, or carboxy-lower alkanoylamino;

R$_2$ is a (C$_1$–C$_6$)alkyl, (C$_2$–C$_6$)alkenyl, (C$_2$–C$_6$)alkynyl, phenyl(C$_1$–C$_6$)alkyl, heteroaryl(C$_1$–C$_6$)alkyl, cycloalkyl(C$_1$–C$_6$)alkyl or cycloalkenyl(C$_1$–C$_6$)alkyl group, any one of which may be optionally substituted by one or more substituents selected from (C$_1$–C$_6$) alkyl, —O(C$_1$–C$_6$)alkyl, —S(C$_1$–C$_6$)alkyl, —OCH$_2$Ph wherein the phenyl group may be optionally substituted, halo and cyano (—CN);

R$_3$ is the characterising group of a natural or non-natural α amino acid in which any functional groups may be protected;

R$_4$ is a group —CHR$^x$R$^y$ wherein R$^x$ and R$^y$ independently represent optionally substituted phenyl or monocyclic heteroaryl rings, which optionally may be linked covalently to each other by a bond or by a C$_1$–C$_4$ alkylene or C$_2$–C$_4$ alkenylene bridge, either of which may be interrupted by an O or S atom;

R$_5$ is hydrogen or a (C$_1$–C$_6$)alkyl group;

or a salt, hydrate or solvate thereof.

2. A compound as claimed in claim 1 wherein the stereochemistry is as follows:

C atom carrying the R$_1$ and X groups—S,

C atom carrying the R$_2$ group—R,

C atom carrying the R$_3$ group—S,

C atom carrying the R$^x$ and R$^y$ groups—R or S.

3. A compound as claimed in claim 1 or claim 2 wherein R$_1$ is methyl, ethyl, hydroxyl, methoxy, allyl, thienylsulphanylmethyl, thienylsulphinylmethyl, thienylsulphonylmethyl or phthalimidomethyl.

4. A compound as claimed in claim 1 or claim 2 wherein R$_2$ is isobutyl, n-pentyl, n-hexyl, n-heptyl, n-octyl, n-nonyl, n-decyl, cyclohexylpropyl, phenylpropyl, phenylpropenyl, 4-chlorophenylpropyl, 4-methylphenylpropyl, 4-methoxyphenylpropyl, pyridine-4-ylpropyl, phenylbutyl, benzyloxybutyl, propyloxymethyl or propylsulphanyl.

5. A compound as claimed in claim 1 or claim 2 wherein R$_3$ is:

(C$_1$–C$_6$)alkyl, benzyl, hydroxybenzyl, benzyloxybenzyl, (C$_1$–C$_6$)alkoxybenzyl, or benzyloxy (C$_1$–C$_6$)alkyl group; or the characterising group of a natural α amino acid, in which any functional group may be protected, any amino group may be acylated and any carboxyl group present may be amidated; or a group -[Alk]$_n$R$_6$ where Alk is a (C$_1$–C$_6$)alkyl or (C$_2$–C$_6$) alkenyl group optionally interrupted by one or more —O—, or —S— atoms or —N(R$_7$)— groups, n is 0 or 1, and R$_6$ is an optionally substituted cycloalkyl or cycloalkenyl group; or a benzyl group substituted in the phenyl ring by a group of formula —OCH$_2$COR$_8$ where R$_8$ is hydroxyl, amino, (C$_1$–C$_6$)alkoxy, phenyl(C$_1$–C$_6$)alkoxy, (C$_1$–C$_6$) alkylamino, di((C$_1$–C$_6$)alkyl)amino, phenyl(C$_1$–C$_6$) alkylamino, the residue of an amino acid or acid halide, ester or amide derivative thereof, said residue being linked via an amide bond, said amino acid being selected from glycine, α or β alanine, valine, leucine, isoleucine, phenylalanine, tyrosine, tryptophan, serine, threonine, cysteine, methionine, asparagine, glutamine, lysine, histidine, arginine, glutamic acid, and aspartic acid; or a heterocyclic((C$_1$–C$_6$)alkyl group, either being unsubstituted or mono- or di-substituted in the heterocyclic ring with halo, nitro, carboxy, ($C_1$–$C_6$)alkoxy, cyano, ($C_1$–$C_6$)alkanoyl, trifluoromethyl ($C_1$–$C_6$)alkyl, hydroxy, formyl, amino, ($C_1$–$C_6$)alkylamino, di-($C_1$–$C_6$)alkylamino, mercapto, ($C_1$–$C_6$)alkylthio, hydroxy($C_1$–$C_6$)alkyl, mercapto($C_1$–$C_6$)alkyl or ($C_1$–$C_6$)alkylphenylmethyl.

6. A compound as claimed claim 1 or claim 2 wherein $R_3$ is a group $CR_aR_bR_c$ in which:

each of $R_a$, $R_b$ and $R_c$ is independently hydrogen, ($C_1$–$C_6$) alkyl, ($C_2$–$C_6$)alkenyl, ($C_2$–$C_6$)alkynyl, phenyl($C_1$–$C_6$) alkyl, ($C_3$–$C_8$)cycloalkyl, the foregoing being subject to the proviso that $R_a$, $R_b$ and $R_c$ are not all hydrogen; or $R_c$ is hydrogen, ($C_1$–$C_6$)alkyl, ($C_2$–$C_6$)alkenyl, ($C_2$–$C_6$) alkynyl, phenyl($C_1$–$C_6$)alkyl, or ($C_3$–$C_8$)cycloalkyl, and $R_a$ and $R_b$ together with the carbon atom to which they are attached from a 3 to 8 membered cycloalkyl or a 5- to 6-membered heterocyclic ring; or $R_a$, $R_b$ and $R_c$ together with the carbon atom to which they are attached form a tricyclic ring (for example adamantyl); or $R_a$ and $R_b$ are each independently ($C_1$–$C_6$)alkyl, ($C_2$–$C_6$) alkenyl, ($C_2$–$C_6$)alkynyl, phenyl($C_1$–$C_6$)alkyl, or a group as defined for $R_c$ below other than hydrogen, or $R_a$ and $R_b$ together with the carbon atom to which they are attached form a 3 to 8 membered cycloalkyl or a 3- to 8-membered heterocyclic ring, and $R_c$ is hydrogen, —OH, —SH, halogen, —CN, —$CO_2$H, ($C_1$–$C_4$) perfluoroalkyl, —$CH_2$OH, —$CO_2$($C_1$–$C_6$)alkyl, —O($C_1$–$C_6$)alkyl, —O($C_2$–$C_6$)alkenyl, —S($C_1$–$C_6$) alkyl, —SO($C_1$–$C_6$)alkyl, —$SO_2$($C_1$–$C_6$)alkyl, —S($C_2$–$C_6$)alkenyl, —SO($C_2$–$C_6$)alkenyl, —$SO_2$($C_2$–$C_6$)alkenyl or a group —Q—W wherein Q represents a bond or —O—, —S—, —SO— or —$SO_2$— and W represents a phenyl, phenylalkyl, ($C_3$–$C_8$) cycloalkyl, ($C_3$–$C_8$)cycloalkylalkyl, ($C_4$–$C_8$) cycloalkenyl, ($C_4$–$C_8$)cycloalkenylalkyl, heteroaryl or heteroarylalkyl group, which group W may optionally be substituted by one or more substituents independently selected form, hydroxyl, halogen, —CN, —$CO_2$H, —$CO_2$($C_1$–$C_6$)alkyl, —$CONH_2$, —CONH ($C_1$–$C_6$)alkyl, —CONH($C_1$–$C_6$alkyl)$_2$, —CHO, —$CH_2$OH, ($C_1$–$C_4$)perfluoroalkyl, —O($C_1$–$C_6$)alkyl, —S($C_1$–$C_6$)alkyl, —SO($C_1$–$C_6$)alkyl, —$SO_2$($C_1$–$C_6$) alkyl, —$NO_2$, —$NH_2$, —NH($C_1$–$C_6$)alkyl, —N(($C_1$–$C_6$)alkyl)$_2$, —NHCO($C_1$–$C_6$)alkyl, ($C_1$–$C_6$) alkyl, ($C_2$–$C_6$)alkenyl, ($C_2$–$C_6$)alkynyl, ($C_3$–$C_8$) cycloalkyl, ($C_4$–$C_8$)cycloalkenyl, phenyl or benzyl.

7. A compound as claimed in claim 1 or claim 2 wherein $R_3$ is benzyl, iso-butyl, t-butyl, 1-benzylthio-1-methylethyl, 1-hydroxy-1methylethyl or 1-mercapto-1-methylethyl.

8. A compound as claimed in claim 1 or claim 2 wherein $R_4$ is a group —$CHR^xR^y$, in which of $R^x$ and $R^y$ groups are independently selected from optionally substituted phenyl, thienyl, furyl, pyrrolyl, imidazolyl, thiazolyl, pyrazolyl, isoxazolyl, isothiazolyl, trizolyl, thiadiazolyl, oxadiazolyl, pyridinyl, pyridazinyl, pyrimidinyl, pyrazinyl and triazinyl.

9. A compound as claimed in claim 8 wherein $R^x$ and $R^y$ are independently phenyl, 2-fluorophenyl, 4-fluorophenyl, 2-pyridyl or 4-chlorophenyl.

10. A compound as claimed in claim 1 or claim 2 in which $R_4$ is optionally substituted 9-H-fluoren-9-yl.

11. A compound as claimed in claim 1 or claim 2 in which $R_5$ is hydrogen.

12. A compound selected from the group consisting of:
$N^4$-[1S-(Benzhydryl-carbamoyl)-2,2-dimethyl-propyl]-2S, $N^1$-dihydroxy-3R-isobutyl-succinamide;

$N^4$-[1S-(9H-Fluoren-9-ylcarbamoyl)-2,2-dimethyl-propyl]-2S,$N^1$-dihydroxy-3R-isobutyl-succinamide;

$N^4$-(1S-{[(4-Chloro-phenyl)-phenyl-methyl]-carbamoyl}-2,2-dimethyl-propyl)-2R,$N^1$-dihydroxy-3R-isobutyl-succinamide;

$N^4$-(1S-{[(4-Fluoro-phenyl)-phenyl-methyl]-carbamoyl}-2,2-dimethyl-propyl)-2S,$N^1$-dihydroxy-3-isobutyl-succinamide;

$N^4$-(1S-{[(2-Fluoro-phenyl)-phenyl-methyl]-carbamoyl}-2,2-dimethyl-propyl)-2S,$N^1$-dihydroxy-3R-isobutyl-succinamide;

$N^4$-[1S-(Benzhydryl-carbamoyl)-2-hydroxy-2-methyl-propyl]-2S,$N^1$-dihydroxy-3R-isobutyl-succinamide;

$N^4$-[1S-(Benzhydryl-carbamoyl)-2-hydroxy-2-methyl-propylcarbamoyl]-2S-methoxy-5R-methyl-hexanoic acid;

$N^4$-[1S-(Benzhydryl-carbamoyl)-2-hydroxy-2-methyl-propyl]-2S,$N^1$-dihydroxy-2-isobutyl-3R-methoxy-succinamide;

$N^4$-[1S-(Benzhydryl-carbamoyl)-2,2-dimethyl-propyl]-2S,$N^1$-dihydroxy-3R-(3-phenyl-ally)-succinamide;

$N^4$-[1S-(Benzhydryl-carbamoyl)-2,2-dimethyl-propyl]-2S,$N^1$-dihydroxy-3R-(3-phenyl-propyl)-succinamide;

$N^4$-{1S-[(Di-pyridin-2-yl-methyl)-carbamoyl]-2,2-dimethyl-propyl}-2S,$N^1$-dihydroxy-3R-isobutyl-succinamide;

2S-Allyl-$N^4$-[1S-(benzhydryl-carbamoyl)-2,2-dimethyl-propyl]-$N^1$-hydroxy-3R-isobutyl-succinamide; and 2S-Allyl-$N^4$-[1S-(benzhydryl-carbamoyl)-2,2-dimethyl-propyl]-$N^1$-hydroxy-3R-octyl-succinamide;

and salts, solvates or hydrates thereof.

13. A process for the preparation of a compound as claimed in claim 1 in which X is a hydroxamic acid group (—CONHOH), which process comprises:

(a) causing an acid of general formula (II)

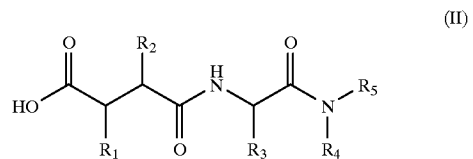

(II)

or an activated derivative thereof to react with hydroxylamine, O-protected hydroxylamine, or an N,O-diprotected hydroxylamine, or a salt thereof, $R_1$, $R_2$, $R_3$, $R_4$, and $R_5$ being as defined in general formula (I) except that any substituents in $R_1$, $R_2$, $R_3$, $R_4$, and $R_5$ which are potentially reactive with hydroxylamine, O-protected hydroxylamine, the N,O-diprotected hydroxylamine or their salts may themselves be protected from such reaction, then removing any protecting groups from the resultant hydroxamic acid moiety and from any protected substituents in $R_1$, $R_2$, $R_3$, $R_4$, and $R_5$; or (b) deprotecting a diprotected hydroxamic acid derivative of formula (IIb)

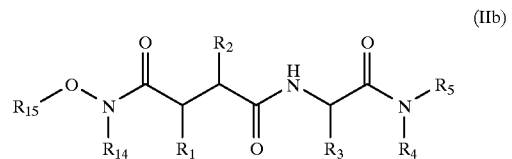

(IIb)

in which $R_1$, $R_2$, $R_3$, $R_4$, and $R_5$ are as defined in general formula (I), $R_{14}$ is an amino protecting group and $R_{15}$ is a hydroxyl protecting group.

14. A process as claimed in claim 13 wherein in step (a) (in the special case where $R_1$ in compound (I) is hydroxy) the hydroxy group $R_1$ and the adjacent carboxyl group are simultaneously protected as a dioxalone of formula (IIa):

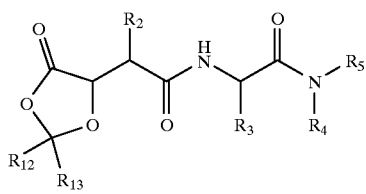
(IIa)

wherein the groups $R_{12}$ and $R_{13}$ are derived from a dioxalone forming reagent, and the dioxalone ring being is opened by the reaction with hydroxylamine to give the required hydroxamic acid derivative of formula (I).

15. A process for the preparation of a compound as claimed in claim 1 in which X is a carboxylic acid group (—COOH) which process comprises coupling an acid of formula (III) or an activated derivative thereof with an amine of formula (IV)

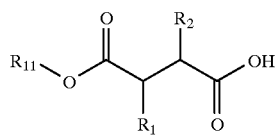
(III)

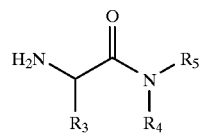
(IV)

wherein $R_1$, $R_2$, $R_3$, $R_4$, and $R_5$ are as defined in general formula (I) except that any substituents in $R_1$, $R_2$, $R_3$, $R_4$, and $R_5$ which are potentially reactive in the coupling reaction may themselves be protected from such reaction, and $R_{11}$, represents a hydroxy protecting group, and subsequently removing the protecting group $R_{11}$ and any protecting groups from $R_1$, $R_2$, $R_3$, $R_4$, and $R_5$.

16. A process as claimed in claim 15 wherein (in the special case where $R_1$ in compound (I) is hydroxy) compound (III) has the formula (V):

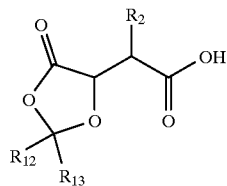
(V)

wherein $R_2$ is as defined in general formula (I) and the groups $R_{12}$ and $R_{13}$ are derived from a dioxalone forming reagent.

17. A pharmaceutical or veterinary composition comprising a compound as claimed in claim 1 or claim 2 together with a pharmaceutically or veterinarily acceptable excipient or carrier.

* * * * *